(12) United States Patent
Aldrich et al.

(10) Patent No.: US 6,355,030 B1
(45) Date of Patent: *Mar. 12, 2002

(54) INSTRUMENTS AND METHODS EMPLOYING THERMAL ENERGY FOR THE REPAIR AND REPLACEMENT OF CARDIAC VALVES

(75) Inventors: William N. Aldrich, Los Altos Hills; Michael V. Morejohn, San Jose; Richard A. Helkowski, Cupertino; Ivan Sepetka, Los Altos, all of CA (US)

(73) Assignee: Cardiothoracic Systems, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/161,079

(22) Filed: Sep. 25, 1998

(51) Int. Cl.[7] .............................................. A61B 18/04
(52) U.S. Cl. ........................ 606/28; 607/99; 607/101; 607/122
(58) Field of Search ........................... 607/96, 98–101, 607/27, 122; 606/28, 29

(56) References Cited

U.S. PATENT DOCUMENTS

| | | | | |
|---|---|---|---|---|
| 4,672,962 A | * | 6/1987 | Hershenson | |
| 5,304,176 A | * | 4/1994 | Phillips | 606/41 |
| 5,376,087 A | * | 12/1994 | Haber et al. | 606/27 |
| 5,433,708 A | * | 7/1995 | Nichols et al. | 604/113 |
| 5,458,596 A | | 10/1995 | Lax et al. | 606/31 |
| 5,514,130 A | * | 5/1996 | Baker | 606/41 |
| 5,766,234 A | * | 6/1998 | Chen et al. | 607/92 |
| 5,769,846 A | * | 6/1998 | Edwards et al. | 606/41 |
| 5,772,590 A | | 6/1998 | Webster, Jr. | 606/374 |
| 5,928,224 A | | 7/1999 | Laufer | 606/27 |
| 5,989,284 A | * | 11/1999 | Laufer | 607/96 |
| 6,267,781 B1 | * | 7/2001 | Tu | 607/113 |

FOREIGN PATENT DOCUMENTS

| | | |
|---|---|---|
| WO | WO 98/18393 | 5/1998 |
| WO | WO 98/19613 | 5/1998 |
| WO | WO 98/26738 | 6/1998 |
| WO | WO 98/32382 | 7/1998 |
| WO | WO 98/35638 | 8/1998 |
| WO | WO 98/44854 | 10/1998 |
| WO | WO/ 98/01076 | 1/1999 |

* cited by examiner

*Primary Examiner*—Roy Gibson
(74) *Attorney, Agent, or Firm*—Thelen Reid & Priest LLP

(57) ABSTRACT

The present invention is methods and devices for improving valve function in a heart. Particularly a device of the present invention comprises a an elongate member having a distal end and a proximal end, a thermal heating member fixed to the distal end of the elongate member, wherein the thermal heating member includes at least one thermal heating element adapted to supply thermal energy to a heart valve structure, and an energy source in communication with the thermal heating element. In use, a thermal heating device of the present invention is inserted into working space proximate the valve to be treated and is used to selectively contract the collagen fibers of the valve structure treated so as to improve the performance and functioning of the valve. Devices are disclosed suitable for use with a variety of access procedures on both beating and non-beating hearts, including: a minimally invasive surgical procedure, a sternotomy, a thoracotomy, an endovascular procedure, and endoscopic procedure, or a percutaneous procedure. Methods and devices are disclosed which are suitable for treatment of a chordae, leaflet, or annulus, as well as devices and methods for the replacement of heart valve with prosthetic valves.

102 Claims, 28 Drawing Sheets

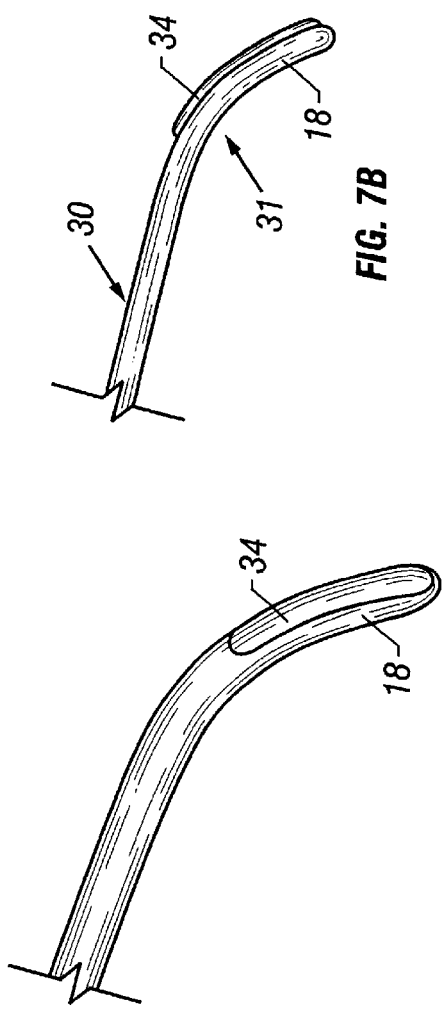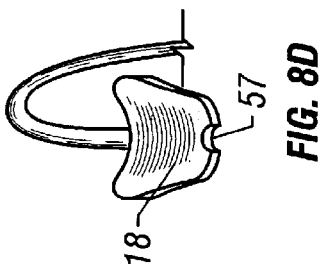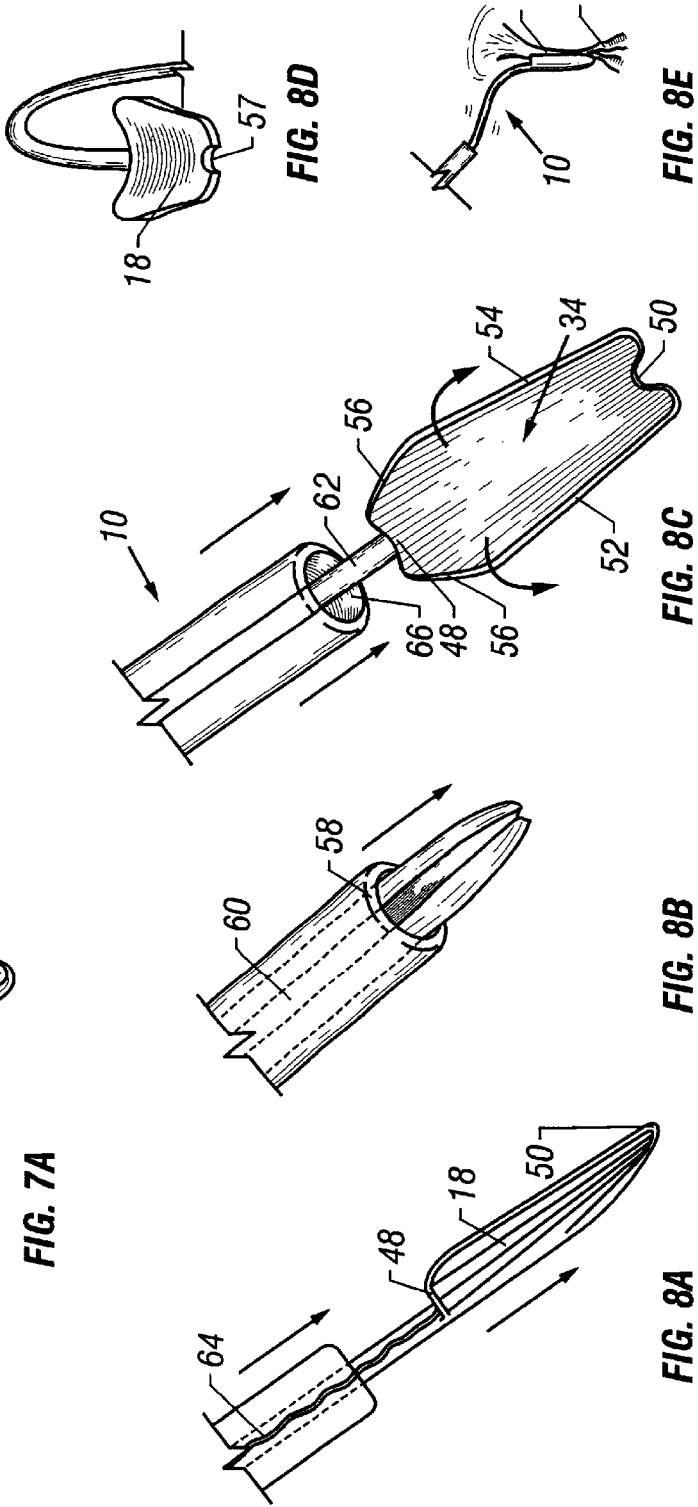

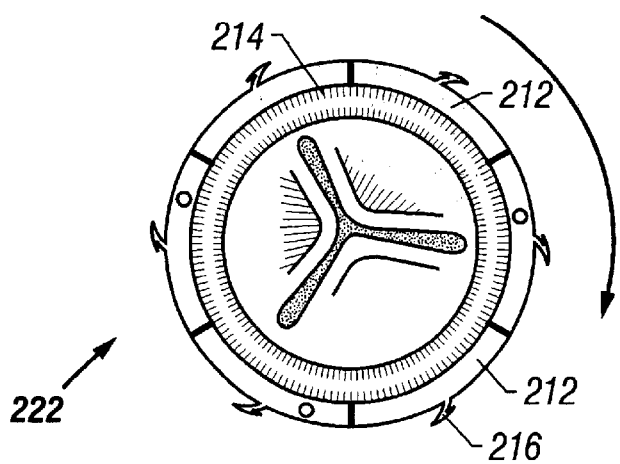
FIG. 22A
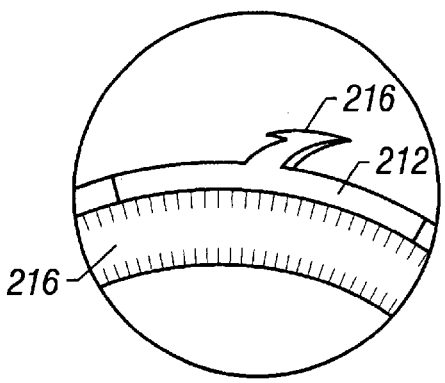
FIG. 22B
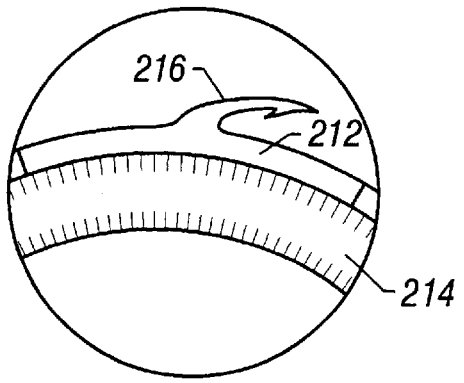     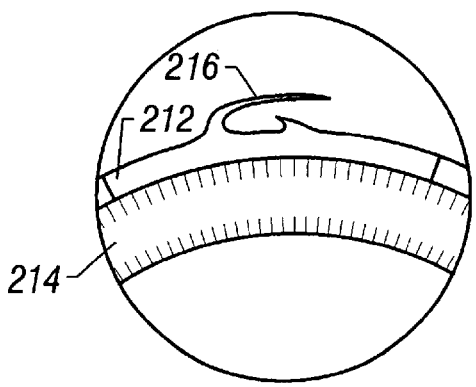
FIG. 22C          FIG. 22D

200
INSTRUMENTS AND METHODS EMPLOYING THERMAL ENERGY FOR THE REPAIR AND REPLACEMENT OF CARDIAC VALVES

FIELD OF THE INVENTION

The present invention relates generally to instruments and techniques for less-invasive cardiac valve repair or replacement, and more particularly to instruments and techniques which employ thermal energy for repairing or replacing cardiac valves.

BACKGROUND OF THE INVENTION

As illustrated in FIGS. 1 and 2 of the attached drawings, the heart has four chambers (the left 11 and right 13 ventricles, and the left 15 and right 17 atria) and four valves (the aortic 19, mitral 21, tricuspid 23, and pulmonary 25 valves) which provide unidirectional flow of blood either from one chamber of the heart to another chamber, or from one chamber to a greater vessel (e.g., aorta 63, superior vena cava 61, inferior vena cava 65, pulmonary artery 67, etc.) of the heart, or from a greater vessel to a chamber. The left 15 and right 17 atria are thin-walled filling chambers which provide only a small amount of pumping force while the left 11 and right 13 ventricles have thick muscular walls for pumping blood out of the heart. The position of the valves is as follows: the mitral valve 21 is between the left atrium 15 and the left 11 ventricle; the aortic valve 19 separates the left ventricle 11 from the aorta; the tricuspid valve 23 is between the right atrium 17 and the right ventricle 13; and the pulmonic valve 25 separates the right ventricle 13 from the pulmonary artery.

The blood circulation process is as follows. Blood circulates from the heart through the body's arterial system to provide oxygen to the body, and then returns with carbon dioxide through the venous system, which culminates in the superior and inferior vena cava at the coronary sinus, and into the right atrium. When the right ventricle is relaxed, blood is pumped by the right atrium through the tricuspid valve into the right ventricle. When the right ventricle contracts, blood is pumped from the right ventricle through the pulmonic valve to the pulmonic trunk and into the lungs where it becomes reoxygenated. The oxygenated blood then returns to the left atrium via the pulmonary veins and is pumped by the left atrium through the mitral valve into the left ventricle. Blood is then pumped by the left ventricle across the aortic valve into the aorta and onto the body's arterial system to repeat the process.

In a normal functioning heart, the four valves operate synchronously as shown with reference to FIGS. 2A and 2B. During systole, when the left and right ventricles contract, the mitral 21 and tricuspid 23 valves close and the aortic 19 and pulmonic 25 valves open to allow blood to flow from the heart to the body and lungs, respectively. During diastole, when the ventricles return to their uncontracted state, the mitral 21 and tricuspid 23 valves open to allow blood to flow from the left and right atria into the left and right ventricles, respectively, while the aortic 19 and pulmonic 25 valves close to prevent blood from flowing from the aorta and pulmonary artery. respectively, back into the heart.

The four heart valves fall into one of two categories. The mitral and tricuspid valves are similar in structure and are referred to as atrioventricular valves, so defined as each separates corresponding atrial and ventricular chambers of the heart. The aortic and pulmonic valves, which are structurally similar to each other but differ greatly in structure from the mitral and tricuspid valves, are known as arterial or semilunar valves.

The atrioventricular valves are each comprised of several collagen-based anatomical components including a number of leaflets or cusps, an annulus, chordae tendineae, and papillary muscles. The leaflets are thin, yellowish-white membranes with fine, irregular edges which define one or more leaflet cusps which converge with adjacent cusps by commisures. The leaflets originate from the valve's annulus which is a fibrous ring around the valve and has a circumference typically in the range between about 8.5 cm and about 10 cm.

The mitral valve has a D-shaped annulus which encircles two leaflets to define a generally bicuspid configuration. The anterior or aortic leaflet is large than the posterior or mural leaflet, the latter having a triscalloped configuration with a large middle cusp between two smaller commissural cusps. The tricuspid valve, as implied by its name, generally has three leaflets consisting of an anterior, a medial (septal), and one (or two) posterior cusps. The commisures of both of these valves have variable depths between the cusps and never reach the annulus resulting in the cusps being only incompletely separated from each other. Upon closure of the atrioventricular valves during systole in a healthy valve, the free edge of each leaflet cusp presses against that of an adjacent leaflet or leaflets, resulting in a secure, fluid-tight closure.

Within the walls of each ventricle are the papillary muscles which act as anchors for tendonous cords, i.e., the chordae tendineae, which are attached at their opposite ends to the leaflets of the mitral and tricuspid valves. The chordae tendineae are divided into three groups. The first two groups of chordae originate from or near the apices of the papillary muscles. They form a few strong, tendinous cords which subdivide into several thinner strands as they approach the leaflet edges. The chordae of the first group insert into the extreme edges of the leaflets by a large number of very fine strands. A major function of the chordae is to prevent the opposing borders of the cusps from inverting. The chordae of the second group insert on the ventricular or under surface of the cusps, approximately at the level of the noduli Albini, tiny nodules at the edge of the cusps. This second group of chordae function as the mainstays of the valves and are comparable to the stays of an umbrella. The third group of chordae originate from the ventricular wall much nearer the origin of the cusps and insert into the underside of the base of the posterior leaflet. These chordae often form bands or fold-like structures which may contain muscle tissue.

The arterial or semilunar valves, i.e., the aortic and pulmonic valves, differ greatly in structure from the atrioventricular valves. The former consists of three pocket-like leaflets, also collagen-based, of approximately equal size. Unlike the artrioventricular valves, the arterial valves do not have a well-defined annulus of fibrous tissue, but instead, the leaflets originate from the arterial wall within which the respective valve sits. For the aortic valve, this is the aorta, and for the pulmonic valve this is the pulmonic artery. The pulmonic valves generally have a diameter ranging from about 19 to 37 mm. The leaflets of these valves expand into three dilated pouches known as the sinuses of Valsalva. The leaflet cusps are largely smooth and thin, and each have, at the center of their free margins, a small fibrous nodule called the nodulus Arantii. On each side of this nodule, along the entire free edge of the cusp, there is a very thin, half-moon-shaped area termed the lunula (hence the name "semilunar"). Unlike the atrioventricular valves, the arterial valves do not have any chordae tendinaea or papillary muscles.

There are various types of acquired diseases or congenital anomalies which can effect one or more of the above-described anatomical components of a cardiac valve such that the valve does not completely or properly open or close. As a result, a valve (i.e., the aortic or pulmonic valve) may restrict blood flow out of the heart during systole, or alternately a valve (i.e., the mitral or tricuspid valve) may allow blood flow back into the heart during diastole. The diseases or anomalies fall within two general categories of pathologies of the valves: stenosis and insufficiency. A stenotic valve is one that does not open properly or allow normal forward blood flow, and an insufficient valve is one that does not close properly or which allows retrograde leakage of blood.

Stenosis of the valve, often characterized by a narrowing of the valve orifice, is typically the result of an acquired disease, most commonly either rheumatic heart disease or arteriosclerosis, but may also result from a congenital defect. With rheumatic heart disease (also known as rheumatic endocarditis), vegetative lesions tend to form on the cusps along the line of closure of the valve. This leads to a fusion of the commisures of the leaflets, reducing the amount of blood flow through the valve. The mitral and aortic valves are the most likely to be affected by this condition, whereas the tricuspid valve is infrequently affected, and the pulmonic valve is rarely affected.

Arteriosclerosis, commonly known as coronary artery disease, is another common cause of stenosis of the cardiac valves. Arteriosclerosis involves a calcification or a build-up of plaque within the coronary arteries which in turn deprives at least a portion of the myocardium of oxygen. The collagenous tissue that forms cardiac valves is highly dependent upon oxygen to maintain its integrity and, when oxygen is not supplied, these tissues will stretch, destroying valvular competency. Particularly, the mitral valve annulus is susceptible to dilation, changing its normal D-shaped or elliptical geometry to a more circular configuration.

Calcification may also occur directly on the valve itself. Unlike the rheumatic lesions, calcium deposits form primarily on the annulus. This may result in a reduction of leaflet mobility and an increase in tension on the chordae which in turn results in elongation of the chordae. Annular calcification frequently occurs in patients with hypertension or metabolic diseases, such as diabetes, but may also result from congenital disorders such as a prolapsed or billowing leaflet, a bicuspid aortic valve (which does not open as widely as a normal aortic valve with three cusps), or disorders of the connective tissue, such as Marfan's syndrome.

The other primary valve pathology, valvular insufficiency, involves improper closure of the valve, causing regurgitation, or the back flow of blood through the valve. As with valvular stenosis, insufficiency of the valves may result from acquired or congenital diseases. Most commonly, this defect is seen in the mitral valve where blood returns through the valve back into the left atrium during systole due to a "prolapse" of the leaflet. Commonly known as mitral valve prolapse (also known as MVP or "click-murmer" syndrome), the leaflets and chordae become affected by a process called myoxmatous degeneration wherein the structural protein and collagen fibers form abnormally causing a thickening, enlargement, or redundancy of the leaflets and chordae. When the ventricle contracts, the redundant leaflets prolapse (flap backwards) into the atrium, allowing backward leakage or regurgitation of blood through the valve opening. If significant, this condition may result in abnormal heart rhythms, endocarditis (infection of the valve), enlargement of the heart, and an imbalance of the autonomic nervous system.

Various surgical techniques have been used to replace, repair or restructure a diseased or damaged cardiac valve. Each technique has its own complexities, advantages, and disadvantages. Most diseased semilunar valves are replaced rather than repaired because their function can be easily simulated with a replacement prosthesis and because the typical types of damage to these valves is not easily repairable. On the other hand, most atrioventricular valves are preferably repaired rather than replaced. This is so because it is difficult to simulate the function of the chordae tendineae of the atrioventricular valves in a replacement prostheses, and often, these valves can be brought to their proper function by the removal of excess valve tissue.

Valve replacement involves excising the valve leaflets of the natural valve, and securing a replacement valve in the valve position, usually by suturing the replacement valve to the natural annulus. The types of replacement valves include mechanical prostheses, biological prostheses, and allografts (transplant of a valve from a donor cadaver, and transplant of the pulmonic valve to the mitral position).

There are currently three widely used types of mechanical prostheses: the Starr-Edwards ball-in-cage valve, the Medtronic-Hall tilting disc valve, and the St. Jude bileaflet valve. As with all valve replacement procedures, replacement with a mechanical valve first involves excising the natural valve from the heart. Especially with the mitral valve, this is a delicate task as excess excision, particularly posteriorly, can result in deficient tissue for suture placement or in complete detachment of the atrium from the ventricle. The natural annulus is then sized with a sizing, instrument. After the size has been determined, a valve is then selected for a proper fit. Proper sizing is important as an oversized replacement valve can cause coronary ostial impingement or tearing of the natural annulus. On the other hand, an undersized valve will reduce flow volume and cardiac output. Next, sutures are placed in the natural valve annulus which has been properly prepared after removal of the leaflets and, in some mitral or tricuspid valve replacement cases removal of, the chordae tendineae. Various suture techniques may be used, including simple interrupted, interrupted vertical mattress, interrupted horizontal mattress with or without pledgets, or continuous, depending on the anatomical valve being replaced, the brand of mechanical valve, and the particular patient anatomy. Regardless of the specific suturing technique employed, this step is crucial to the outcome of the replacement procedure, requiring accurate and flawless suturing. After placement in the natural annulus, the same sutures are placed through the mounting cuff, the valve is seated into the annulus, and the sutures are tied and with the excess suture length cut.

Although mechanical valves have proven to be extremely durable and can be expected to last from 20 to 40 years, they all require life-long anticoagulation with blood thinners to prevent clot formation on the valve surfaces. These replacement valves have the further disadvantage in that the mounting cuffs or rings occupy space, narrowing the effective orifice area of the valve and reducing cardiac output.

Biological prosthetic valves, such as those processed from pigs (porcine) or cows (bovine), have the advantage of not requiring the patient to take life-long anticoagulation medication or requiring a mounting prostheses. However, the average life expectancy for such bioprostheses is only from about 8 to 10 years. Therefore, bioprostheses are primarily used in older patients or in patients who cannot tolerate blood thinners. Recently, valves from human cadavers have been used in younger patients to avoid the need for anticoagulation medication, however, the availability of human grafts is limited with long-term outcomes still unknown.

For these reasons, it is sometimes preferable to repair rather than replace a cardiac valve. Valve repair techniques which involve the removal or reduction of some portion of the valve include: annuloplasty (contracting the valve annulus), leaflet resection (narrowing the valve leaflets), and shortening the mitral or tricuspid valve chordae tendineae. Prosthetic ring annuloplasty is commonly performed to reduce a dilated valve annulus, most commonly in the mitral valve. This procedure involves suturing a semirigid ring to the natural annulus of the valve. The selective rigidity of the ring allows the surgeon to reshape the annulus to its normal elliptical configuration while maintaining an optimal orifice area.

Resection of the leaflet is performed when a leaflet is prolapsed due to an elongated or ruptured chordae. Repair is achieved by excision of a portion of the leaflet. The open portion of the leaflet is then sutured closed and stay sutures are placed around the normal chordae adjacent to the prolapsed portion of the leaflet.

An elongated chordae can be corrected by folding the excess length of the chordae into an incised trench made in the papillary muscle. After the trench is made a suture is placed through half of the trench, around the elongated chordae, and then through the other half of the trench. Enough traction is placed on the suture so that the excess length of the chordae is pulled into the trench in the papillary muscle, thus wedging the resection of the papillary muscle to shorten the chordae at which point the trench is sutured closed, trapping the excess chordae inside.

The above valve repair techniques, when properly performed, can result in low operative mortality, improvement in ventricular function low incidence of thromboembolism, low incidence of reoperation, and lasting(g improvement in hemodynamics. However, these procedures can be extremely complex, particularly in patients requiring more than one valve repair procedure, such as a combination of annuloplasty and leaflet resection. Often, only the most highly skilled cardiac surgeons are successful at these valve repair procedures. A particularly prevalent cause of reoperation in valve repair procedures is caused by shortening of the chordae which results in a poor fit of the valve or valve leaflets and may result in prolapse or regurgitation of the valve.

Conventionally, the repair or replacement of a heart valve is accomplished through a median sternotomy (most typically for an aortic valve procedure) or major thoracotomy (most typically for a mitral valve procedure), requiring(g general anesthesia and total cardiopulmonary bypass (CPB) with cardioplegic arrest. These procedures are highly traumatic and have significant complications associated with the median sternotomy or major thoracotomy, resulting in a prolonged, painful, and expensive recovery. Such procedures tend to involve a large number of instruments and sutures, making access via an invasive incision unavoidable. Additionally, typical conventional valve procedures require the patient to be on a CPB "pump run" and have cross-clamping of the aorta (the ill effects of both which are well known and documented) for at least an hour in replacement procedures and about an hour and a quarter for repair procedures. These times arc further increased for surgeries involving more than one repair or replacement procedure and/or the repair or replacement of the repair or replacement of more than one valve.

Less-invasive and endoscopic devices and methods have been developed which eliminate the need for an invasive incision. However, small or endoscopic incision sites and instrumentation increase the complexity of the surgery and increase the already lengthy pump runs and cross-clamp times.

What is needed, therefore, are devices and methods for carrying out heart valve replacement and repair, as well as other procedures in the heart, which eliminate the complexities associated with current techniques, reduce the pain and trauma to the patient, and reduce the time which the patient is on CPB and cross-clamping. The present invention fulfills these needs, and provides further related advantages, as will become apparent from the following description and accompanying drawings of the invention taken in conjunction with the appended claims.

SUMMARY OF THE INVENTION

The present invention provides devices and methods for performing surgical procedures which involve the thermal contraction or shrinking of collagen-based tissue in the heart, and more particularly which involve the thermal reduction of collagen-based tissue of the heart valves to improve the function of a diseased or defective valve.

Collagen molecules consist of three polypeptide chains arranged in a parallel triple-helix. The individual polypeptide chains are called alpha-chains, and each is approximately 1000 amino acid units in length. This results in an average diameter of 14 Å and an average length of about 300 nm for a single collagen molecule. The helical conformation of each chain is dependent on the fact that every third unit is glycine with hydroxyproline and proline recurring very frequently. Cross-linking occurs between the sides of the collagen molecules. These intermolecular cross links provide collagen tissue with the unique physical properties of high tensile strength and substantial elasticity.

When subject to elevated temperatures, the collagen cross links rupture resulting in an immediate contraction or shrinking of the collagen fibers. This shrinkage takes place in a direction parallel to an axis of collagen fibers and can result in as much as a ⅔ reduction in the fibers' original length. Additionally, the diameter of the individual fibers increases greatly, over four fold, without changing the structural integrity of the tissue.

The thermal shrinking of collagen connective tissue is a known technique in orthopedic applications, such as in the repair of ligaments and joint capsules. U.S. Pat. No. 5,458,596 to Lax et al discloses the use of radiofrequency (RF) energy for the controlled, non-ablative thermal shrinking of collagen-based tissue in orthopedic applications. What has not previously been contemplated, however, is the use of non-ablative thermal energy to shrink or contract collagen-based tissue in the heart, and particularly for the repair of diseased or defective heart valves requiring the removal or contraction of tissue, or for facilitating the attachment of a replacement valve.

Accordingly, a general object of the present invention is to provide methods and instruments for the application of thermal energy to a tissue site in the heart which is comprised of collagen.

The teachings of the present invention include an apparatus for supplying thermal energy to a diseased heart valve structure comprising an elongate member having a distal end and a proximal end, including a thermal heating member fixed to the distal end of the elongate member, and at least one thermal heating element adapted to supply thermal energy to a diseased heart valve structure disposed on the thermal heating member. An energy source in communication with the thermal heating element is also provided for supplying thermal energy to a target location on the valve structure. Preferably, the thermal heating element is an electrode in electrical communication with the power source.

An apparatus for providing thermal energy to a valve structure may also include additional components, including: an integrally formed endoscope configured to allow visualization of an area of interest of the diseased heart valve structure; a vacuum lumen adapted to connect an external vacuum source with a vacuum port disposed on the distal end of the elongate member; and a fiber-optic illuminator adapted to provide illumination of the diseased heart valve structure. Generally, the thermal heating member includes at least one thermal heating element and may include one or more additional structures such as described above.

In a preferred configuration of the present invention, the apparatus includes a controller configured to selectively control the intensity and duration of thermal energy supplied to the thermal heating element; a temperature sensor adapted to monitor the temperature of the thermal heating element; and a feedback control device configured to receive temperature data from the temperature sensor and adjust the supply of energy to the thermal heating element so as to maintain the temperature of the thermal heating element within a preselected temperature range. In this manner, the treatment temperature may be controlled to prevent ablative damage to the treated tissue.

A variety of configurations are appropriate for the thermal heating member, including a transverse groove sized to accommodate a diseased chordae wherein the at least one thermal heating element is disposed on an inner surface of the groove; a hook member sized to engage the chordae, wherein the at least one thermal heating element is disposed on an inner surface of the hook member. The thermal heating member may be configured to be conformable to allow adjustment of the device for different clinical applications.

In one embodiment, the apparatus of the present invention is configured to be endoscopically inserted to region of interest and includes a trocar insertion sleeve configured to slidably receive the elongate member and the thermal heating member, wherein the heating member is adapted to be disposed within the trocar insertion sleeve. In one configuration, the apparatus includes a thermal heating member comprising a flexible panel member configured to be rolled lengthwise when disposed within the trocar insertion sleeve. The device may also be made steerable to facilitate insertion and manipulation of the device.

The teachings of the present invention include an apparatus configured to supply thermal energy to a diseased annulus wherein the thermal heating member comprises an annular configuration sized to approximate the circumference of a diseased annulus. In such a configuration, the thermal heating member includes a plurality of thermal heating elements disposed about a circumference of the annular configuration as well as additional structures. Alternatively, the apparatus may be configured to allow beating heart repair of a diseased annulus or leaflet without interfering with the functioning of the treated valve. A preferred embodiment of an apparatus for repairing a diseased valve structure is configured to be endovascularly inserted in a contracted configuration to a region of interest proximate a valve to be treated. The apparatus configured to be expanded for treatment of the valve structure.

Another embodiment of a device for providing thermal energy to a diseased valve structure comprises a thermally conductive suture configured for installation in the valve structure to be treated, and a power source in communication with the thermally conductive suture.

The teachings of the present invention include devices for the replacement of a diseased heart valve utilizing thermal energy supplied to the annulus of the diseased valve. A preferred device comprises an elongate member having a distal end and a proximal end, a thermal heating member configured to provide thermal energy to the annulus of a diseased heart valve fixed to the distal end of the elongate member, and at least one thermal heating element disposed on the thermal heating member. The device also requires an energy source in communication with the thermal heating element. The device may also include a valve holder configured to fix a prosthetic valve to the distal and of the elongate member.

The present invention also includes methods of repairing a diseased valve using the application of thermal energy to the diseased valve structure. A preferred method comprises the steps of a) providing a working space proximate the diseased heart valve structure, and b) providing non-ablative thermal energy to the diseased valve structure so as to selectively contract the diseased heat valve structure. Preferably, the step of providing non-ablative thermal energy to the diseased valve structure comprises the steps of contacting the diseased heart valve structure with a thermal heating element, and providing thermal energy from the thermal heating element to the diseased valve structure so as to selectively contract the diseased heart valve structure.

The step of contacting the valve structure with the thermal heating element may comprises a number of alternate methods, including installing at least one thermally conductive suture in the valve structure to be treated. The valve structure contacted includes a diseased chordae, a diseased annulus, or a diseased or misfitting valve leaflet.

In a preferred method of the present invention, the heart function is monitored concurrently with treating the diseased valve structure so as to receive feedback on the treatment effect. In one method, the monitoring device comprises a transesophegial echocardiography device, the method including the additional step of installing the device so as to monitor the functioning of the diseased heart valve.

A number of access procedures are suitable for use with the teachings of the present invention, including: a thoracotomy, a sternotomy, a mini-thoracotomy, a thorascopic access procedure, a mini-sternotomy, a sub-xyphoid access procedure, a xyphoid access procedure, and an endovascular access procedure. The teachings of the present invention are suitable for use with both beating heart and stilled heart procedures.

The teachings of the present invention include methods for replacing a diseased valve using thermal energy applied to the valve annulus. A preferred method of replacing a diseased heart valve comprises the steps of a) providing a working space proximate the diseased heart valve; b) excising the leaflets of the natural heart valve; c) inserting the prosthetic heart valve into the annulus; d) contacting the annulus with a thermal heating element; e) providing thermal energy from the thermal heating element to the annulus to selectively contract the annulus about the prosthetic heart valve; and f) continuing to provide thermal energy to the annulus until the prosthetic heart valve is securely engaged within the annulus.

BRIEF DESCRIPTION OF THE DRAWINGS

FIG. 7 is an alternate configuration of a heating member for supplying thermal energy to a collagen based body structure.

FIGS. 8(A–E) illustrate an alternate configuration of an apparatus for endoscopically supplying thermal energy to a collagen based body structure.

FIGS. 22(A–D) show a number of alternate configurations for retaining means configured to prevent accidental dislodgement of the replacement valve from the annulus.

DETAILED DESCRIPTION OF PREFERRED EMBODIMENTS

Figure 1:
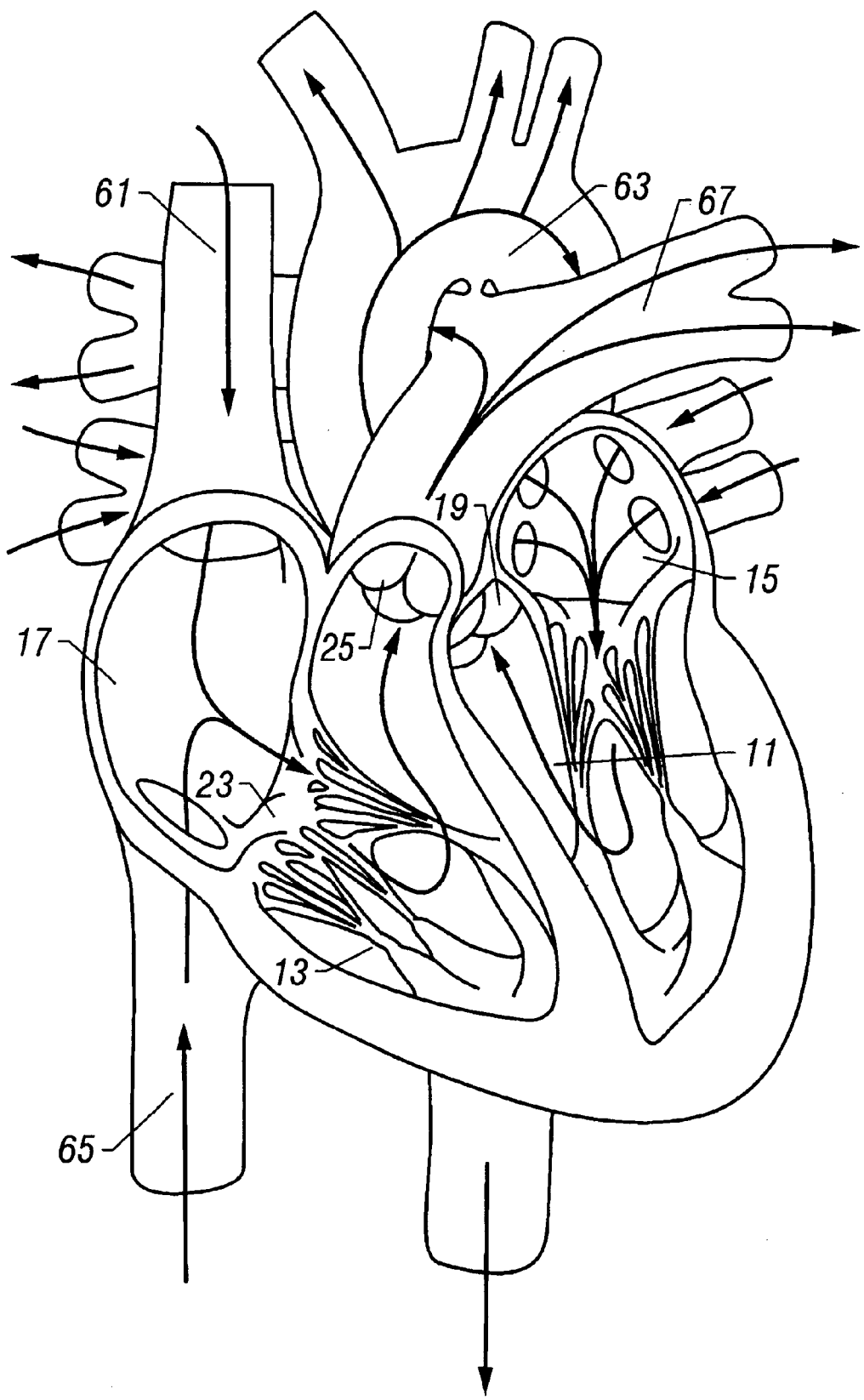
FIG. 1 is a schematic cross-sectional illustration of a human heart.
Figure 2A:
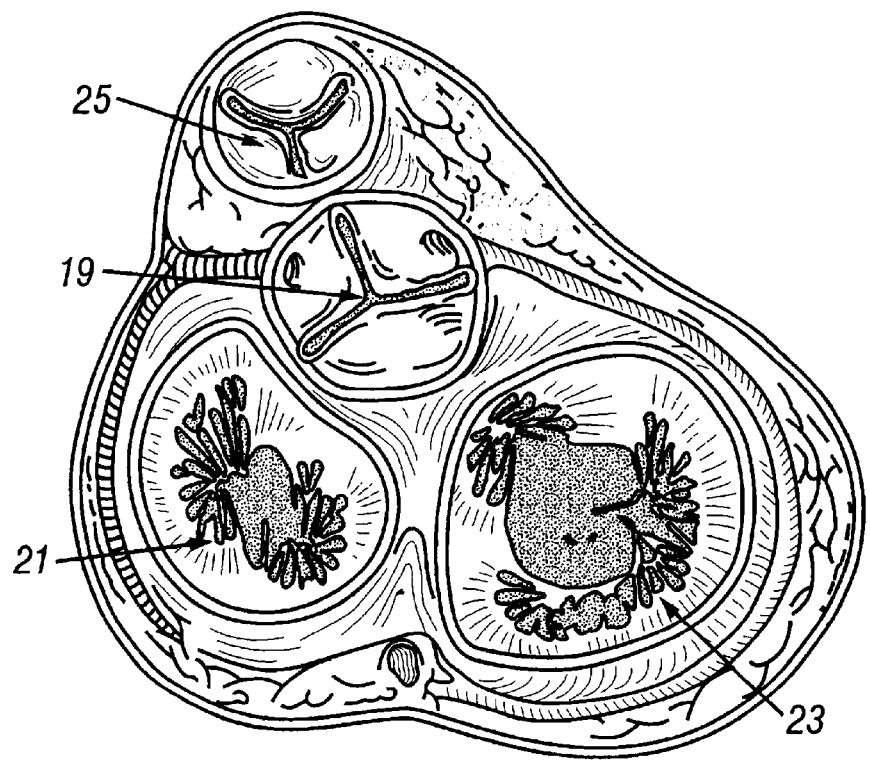
FIG. 2A is a transverse cross-sectional top view of the four valves of the heart during diastolic function.
Figure 2B:
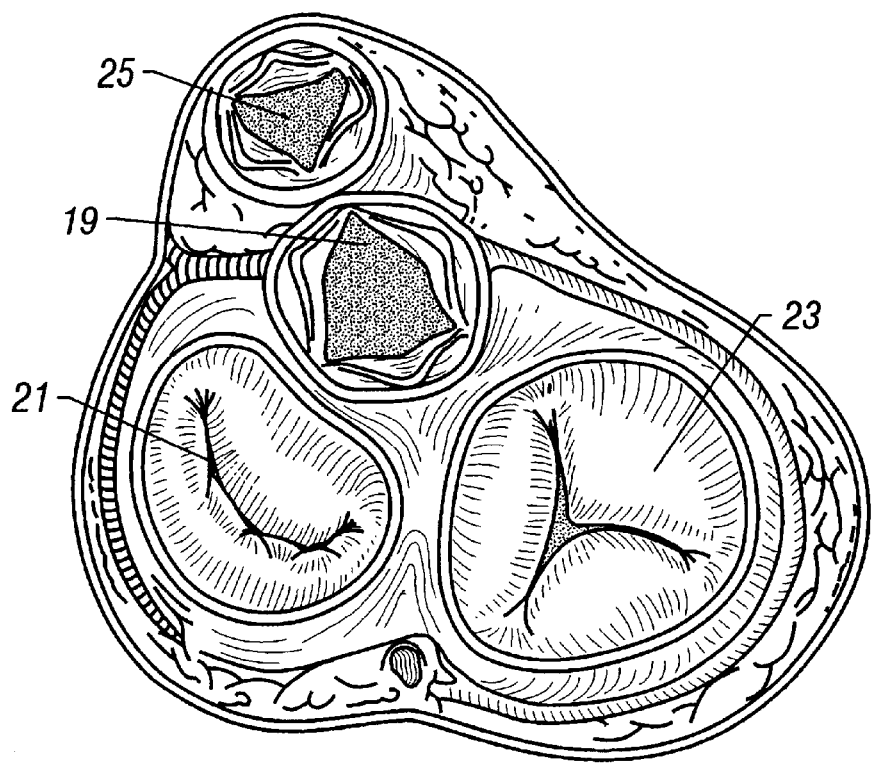
FIG. 2B is a transverse cross-sectional top view of the four valves of the heart during systolic function.
Figure 3C:
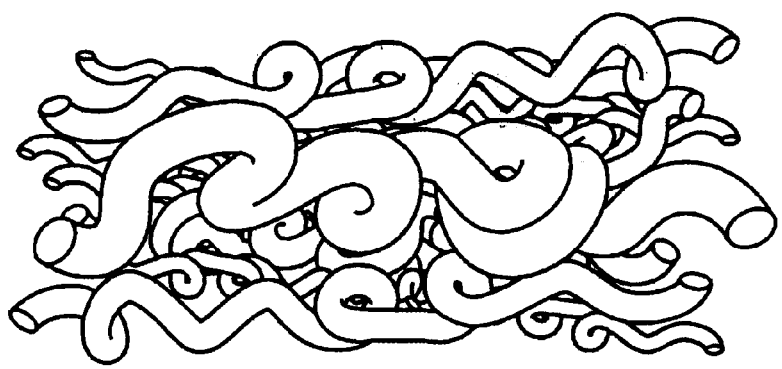
FIG. 3C shows the fibers after exposure to thermal energy.
Figure 3B:
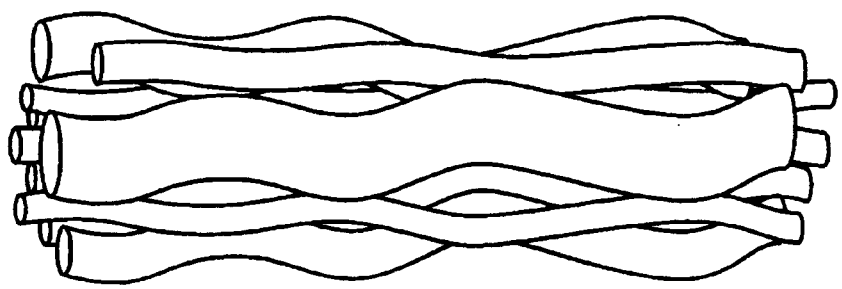
FIG. 3B shows the effects of thermal energy on the cross linking of the collagen fibers.
Figure 3A:
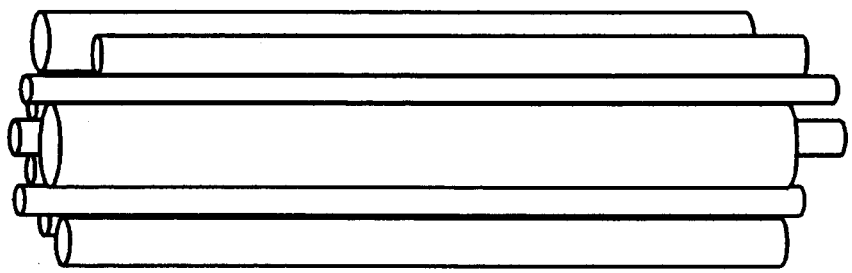
FIG. 3A is a microscopic view of the orientation of collagen fibers.

Exemplary, preferred embodiments of the devices and methods of the present invention will now be described in detail. Although the following description focuses primarily on the mitral valve in the context of valve repair surgery and on the aortic valve in the context of valve replacement surgery, the techniques and instruments of the present invention are not intended to be limited to such, and may be used for the repair or replacement of any heart valve. Considerations such as the valve to be operated on, the indication to be treated (e.g. leaflet prolapse, annulus dilation, leaflet calcification, etc.), the point of access (e.g., thoracic cavity, neck, groin, etc.), the type of access (e.g., direct-vision, minimally invasive, endoscopic, or percutaneous), and whether the procedure is performed on a stopped, partially assisted, or beating heart will dictate the specific technique and instrument to be used.

Referring now to the drawings, with like reference numbers referring to like elements of the invention, there are shown various embodiments of the present invention for selectively delivering thermal energy for the controlled contraction of heart valve tissue comprised of collagen fibers. Generally, FIGS. 4–18 illustrate devices and methods for repairing a defective or diseased valve having excess tissue which requires removal or reduction. FIGS. 19–23 illustrate embodiments for placing a mechanical replacement valve in the heart. FIGS. 24–29 illustrate the use of thermally conductive sutures to selectively reduce collagen-based tissue in the heart for the repair or replacement of a diseased heart valve.

Turning now to a discussion of techniques and devices for the repair of valves, FIGS. 4–18 illustrate devices and methods for delivering thermal energy, such as radio frequency (RF) energy, to collagen-based components of a valve, including the leaflets annulus, and chordae tendinaea (the latter two applying to the mitral and tricuspid valves only). Such devices are useful for reducing or shrinking excess valvular tissue that would otherwise need to be excised or foreshortened by conventional means in order for the valve to properly function. These devices may be configured to deliver thermal energy to a surface of a prolapsed or billowing leaflet, an elongated chordae, or a dilated annulus.

Although the specific discussion that follows describes the use of radio frequency (RF) energy, a variety of other thermal energy sources can be used with the present invention including but not limited to microwave, coherent light, and thermal transfer. Other means of contracting collagenous tissue include ultrasonic energy and coherent light. The principal requirement is that the energy source be appropriate for low level application of non-ablative energy to the surface of the collagen body and be of sufficient degree to cause rupture of the collagen cross links and a subsequent contraction or shrinking of the collagen fibers. Temperatures ranging from 40 to 90° C. have been found to work best for achieving maximum contraction of the treated collagen fibers. Tower temperatures do not provide maximum disassociation and contraction of the collagen fibrils while greater temperatures cause undesirable destruction and ablation of the collagen fibrils.

Figure 4A:
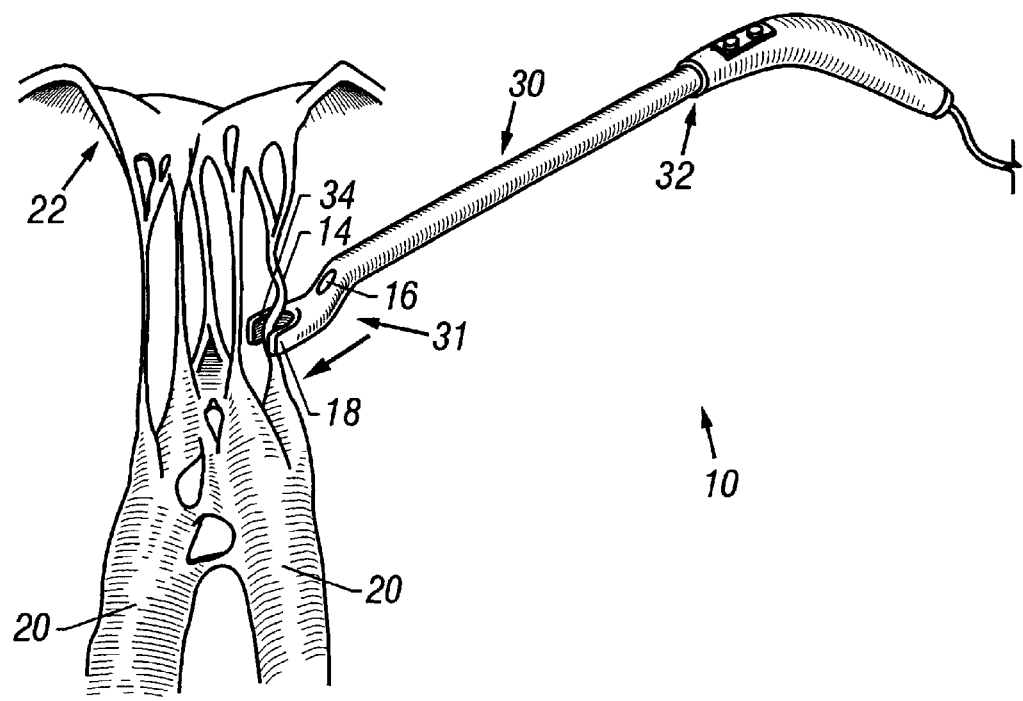
FIG. 4A shows an apparatus for supplying thermal energy to a collagen based body structure in use to remodel an elongated chordae.

As shown in FIG. 4A, the apparatus 10 for supplying non-ablative thermal energy to a collagenous body structure comprises an elongate member 30 having a distal end 31 and a proximal end 32. The distal end 31 of the apparatus 10 of FIG. 4 is particularly adapted to supply thermal energy directly to an elongated chordae 14. Preferably, the distal end 31 comprises a horseshoe shaped heating member 18 having a transverse groove including one or more heating elements 34 located on an inner surface of the transverse groove. The groove is preferably sized to fit about one or more chordae 14 to be treated. The heating elements 34 of the apparatus supply thermal energy to the chordae 14 from three sides. A transverse groove having a width of approximately 2 mm is preferable for most chordae treatment applications. The elongate member 30 may also include a lumen 16 having a distal opening proximate the heating member 18. The lumen 16 may be configured to receive an imaging apparatus, an optical lens arrangement, or other endoscopic visualization devices to provide visual feedback from the treatment site. Alternatively, the lumen 16 may be connected in vacuum communication with a vacuum source at a distal end of the lumen 16. During treatment, the vacuum removes, blood, or other debris from the treatment site and provide a clear surgical field.

Figure 4B:
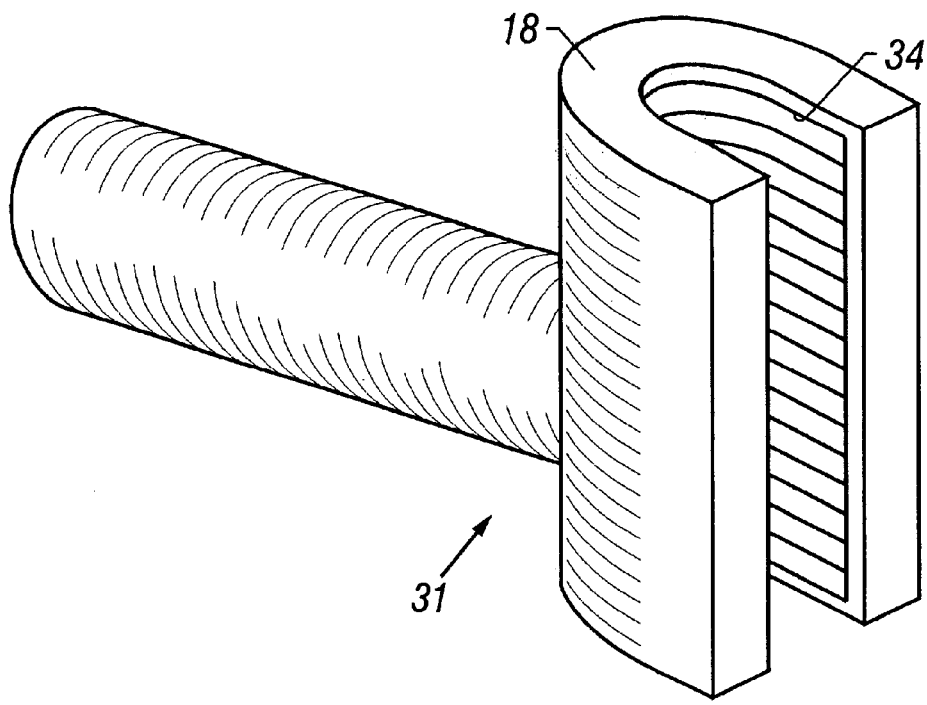
FIG. 4B is a perspective view of a heating member of the present invention.
Figure 4C:
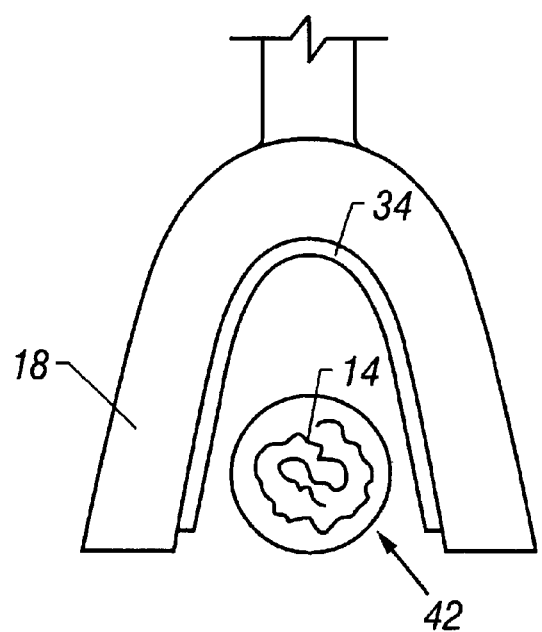
FIG. 4C is a plan view of a heating member of the present invention shown supplying thermal energy to a chordae fiber.

The device shown in FIG. 4A is most appropriate for supplying thermal energy to a short segment of an elongated chordae however, a longer configuration as shown in FIG. 4B is preferably used to supply thermal energy to longer segments of an elongated chordae 14. The preferred configuration of the distal end 31 of the apparatus 10 will depend primarily on the clinical indications; including the method of access that is chosen for the valve remodeling procedure and the physical characteristics of the elongated chordae 14. FIG. 4C shows another configuration of the distal end 31 of the apparatus 10 wherein the distal end 31 includes a heating member 18 having a substantially "V"-shaped transverse groove. An open end 42 of the heating member 18 is configured to accommodate the chordae 14 during treatment. As shown in FIG. 4C, a one-piece heating element 34 may be provided on the interior surface of the transverse groove to provide thermal energy to the chordae 14.

The device of FIG. 4A further includes a handle member 36 shaped to conform to the surgeon's grip so as to provide comfortable operation and manipulation of the apparatus 10. The handle member 36 may also include a manually operable heating control 37 which can selectively control the amount of thermal energy supplied to the diseased portion of the valve. Furthermore, elongate member 30 may be malleable to allow bending and manipulation of the elongate member 30 during the procedure to more easily access and treat the diseased valvular tissue.

An important aspect of the present invention is the use of non-ablative thermal transfer to selectively shrink a localized area of collagen within the valve structure. It is undesirable to ablate or destroy the collagen fibrils of the valve structure because of the negative impacts on the cardiac performance and flow characteristics of the valve, e.g., permanent damage may result requiring valve replacement. In order to prevent the temperature of the treatment site to exceed suitable parameters, a feedback control system may be used to monitor the tissue temperature to prevent excessive treatment of the valve structure. For example, a microprocessor, the structure and function of which is well known in the art, may be included in an apparatus of the present invention. The microprocessor is configured to receive temperature data from a temperature sensor situated at the site of the treated tissue or at the thermal heating element. Using the received temperature data, the microprocessor continually adjusts the supply of thermal heating energy to the treated valve tissue in order to maintain the treatment temperature within clinically determined limits.

In another embodiment of the present invention, an electrolytic or thermally conductive fluid or gel, such as saline or blood, may be used to prevent direct contact between the thermal heating element and the treated collagen tissue of the valve structure. In this manner, an even temperature gradient may be established which prevents localized "hot spots" in the treatment area which may cause unwanted ablation of the collagen tissue. In addition, "cold spots" are avoided wherein the collagen tissue receives less thermal energy, resulting in less contract of the tissue than the surrounding tissue. These "cold spots" can result in incomplete or uneven treatment of the collagen tissue and improper fit of the valve. The electrolytic fluid or gel may be applied either to the distal end of the apparatus for supplying thermal energy to a collagen based body structure directly or a separate lumen (not shown) may be used to provide a source of electrolytic fluid or gel to the site of tissue treatment. The fluid may be left in place following treatment or a return lumen (not shown) may be provided so that a continuous supply of electrolytic fluid is cycled across the treatment site. A preferred method of the present invention comprises the additional step of providing a thermally conductive fluid to the valve structure to be treated prior to providing thermal energy the valve structure.

Another means of preventing localized variations in the treatment temperature of the collagen tissue is to include an insulating layer over the heating element 34. In a preferred embodiment, the heating element 34 is an electrode configured from platinum, gold, stainless steel, or some other noble metal well known in the art. The heating element may be insulated from the tissue surface with a partially conductive material which evenly distributes thermal energy from the thermal heating element to the treated tissue surface. The insulating layer serves to keep the thermal heating element in a spaced apart relationship with the tissue surface to be treated.

Figure 5:
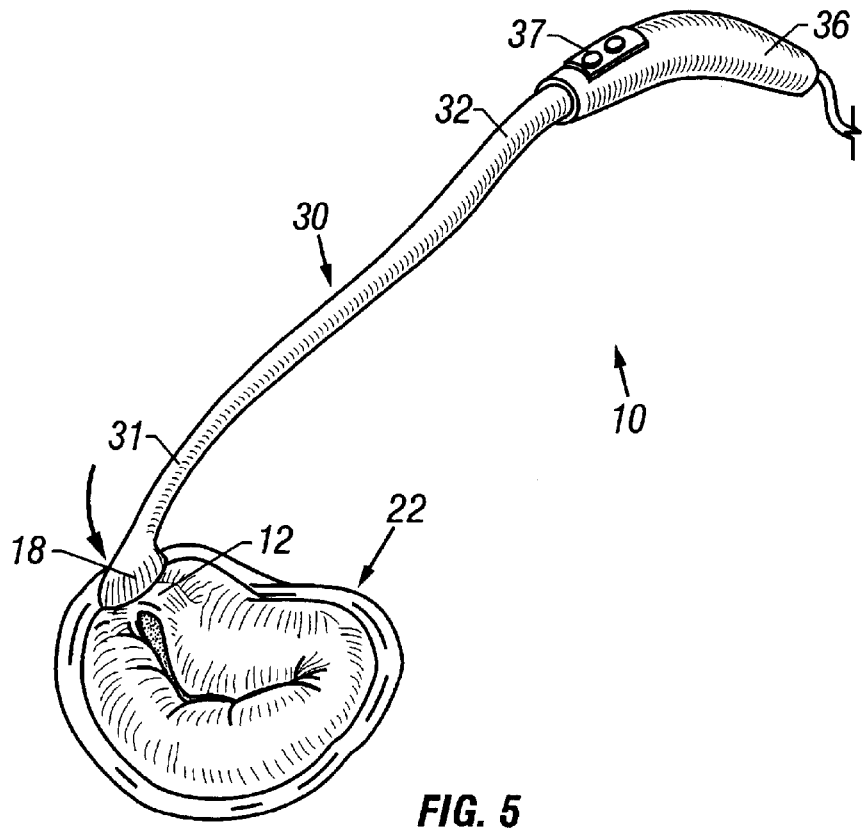
FIG. 5 shows an apparatus for supplying thermal energy to a collagen based body structure in use to remodel an "billowing" valve leaflet of a diseased mitral valve.

FIG. 5 shows an alternate configuration of the apparatus 10 wherein the distal end 31 includes a flattened heating member 18 having one or more heating elements 34 disposed on a distal surface of the heating member 18. The heating member 18 is particularly configured to supply thermal energy directly to a "billowing" leaflet of a diseased heart valve 22. In the example shown in FIG. 5, the heating member 18 of the apparatus 10 is shown applied directly to the surface of the mitral valve 22 so as to repair a billowing portion 12 of the diseased valve 22.

Figure 6A:
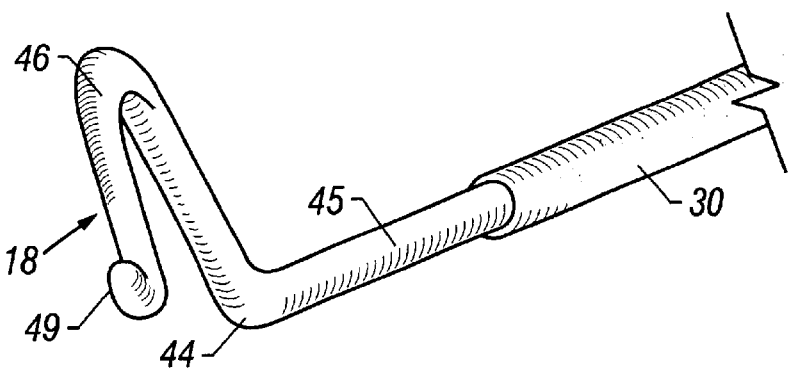
FIG. 6A is a perspective view of an apparatus for supplying thermal energy to a collagen based body structure having a specially configured heating member for supplying thermal energy to a chordae fiber.
Figure 6B:
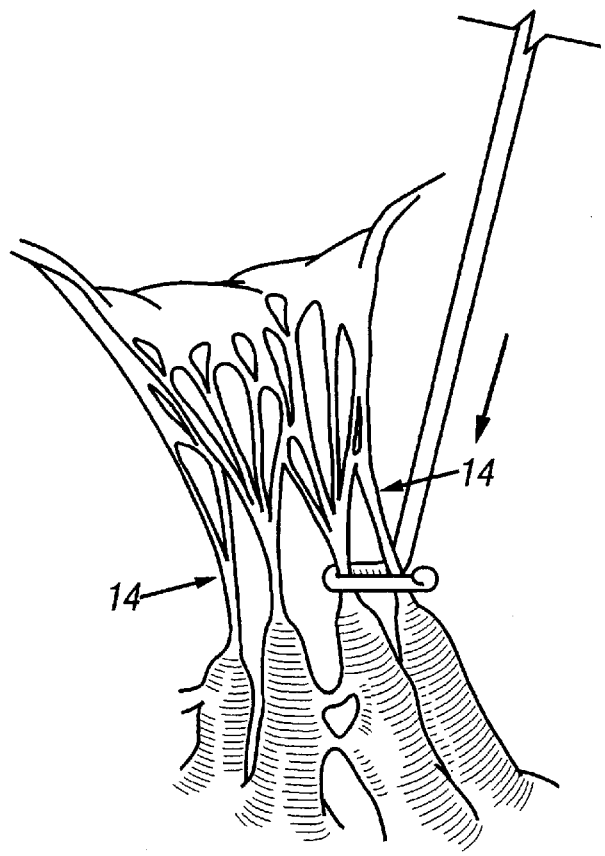
FIG. 6B shows a device of FIG. 6A in use to treat chordae fibers of a disease heart valve.
Figure 6C:
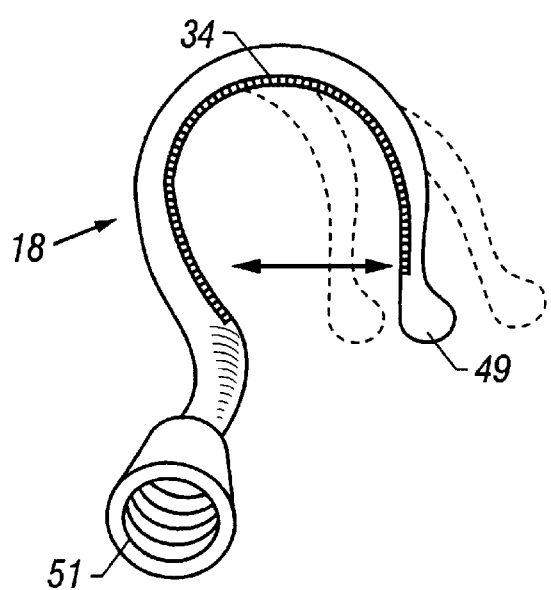
FIG. 6C is a detail view of the heating member of FIG. 7A wherein the heating member is conformable for varying chordae geometrics.

FIGS. 6(A–C) show an alternate configuration for the heating member 18 of the apparatus 10. This configuration is suitable for application of thermal energy directly to the chordae 14 but may not be the most suitable means of applying thermal energy to a flat surface, such as a valve leaflet or valve annulus. As shown in FIG. 6A, the heating element is preferably a tubular member having a shaft portion 45 configured having a first bend 44 of approximately 90° and a second "U"-shaped bend 46 wherein the plane defined by bend 46 is approximately perpendicular to shaft portion 45. As seen in FIG. 6B the function of the offset between the first 44 and second 46 bends is to provide a configuration wherein the apparatus 10 may be inserted directly through the annulus of the valve to provide thermal energy to the chordae tendineae 14 while maintaining the elongate member 30 of the instrument substantially parallel with the axis of the chordae 14 to be treated. As shown in FIG. 6C, the heating member 18 can also be made substantially flexible to accommodate a variety of chordae sizes and application sites.

In use, the apparatus of FIG. 6 is situated relative to the chordae to be treated as shown in FIG. 6B. The heating element 18 is slid along the length of the diseased chordae while supplying thermal energy to the diseased chordae. The heating member 18 may also be adjustable or removable as shown in FIG. 6C so that a variety of heating member configurations may be used to ensure a precise fit between the chordae treated and the interior geometry of the curved portion of the member 18. To this end, the heating member may include a collar 51 which allows detachment of the member 18 from the distal end of the elongate member 30. The collar 51 may include threads or other fastening means to secure the collar 51 to the elongate member 30. The heating member 18 also preferably includes an atraumatic tip portion 49 which prevents trauma to the treated collagen tissue while allowing precise separation and selection of the particular chordae to be treated. The "U"-shape of the heating member 18 may also be varied to increase the length of the two legs of the "U" to allow treatment of multiple chordae in a single pass of the heating member 18.

FIG. 7 shows another configuration of the heating member 18 of the apparatus 10 for supplying thermal energy to a collagen based body structure wherein the heating member 18 comprises a curved portion at the distal end of the elongate member 30. The outermost surface of the curved portion comprises a heating element 34 configured to supply thermal energy to the chordae surface. The heating element 34 may also be configured having a concave groove (not shown) so as to more evenly provide thermal energy to the chordae surface during treatment.

FIGS. 8A–E is an alternate embodiment of the apparatus 10 for supplying thermal energy to a collagen based body structure wherein the apparatus 10 is configured for endoscopic or endovascular insertion to the region of interest. The apparatus 10 includes a heating member 18 comprising a flattened panel member having a distal end 50, a proximal end 48, and a first 52 and second 54 lateral edge. The first 52 and second 54 lateral edges of the heating member are slightly curved upward when in a relaxed position as best seen in FIG. 8A. The concave front profile of the heating member 18 can be seen with reference to FIG. 8D, wherein the upward curve of the first 52 and second 54 lateral edges is readily apparent. The heating member 18 is configured to be flexible enough so that the member 18 may be rolled lengthwise and disposed within an internal lumen 66 of a trocar insertion tube 60 as best seen in FIG. 8C. Distal movement of the heating, member 18 relative to the trocar insertion tube 60 causes the member 18 to exit the tube 60. Once free of the tube 60, the natural resilience of the member 18 causes the member to unfold into the configuration shown in FIG. 8A.

As best seen in FIG. 8D and FIG. 8C, the proximal end 48 of the heating member 18 is configured having curved corners 56 which gently urge the heating member 18 back into its curled configuration when the member 18 is withdrawn back into the trocar insertion tube 60. The distal edge 58 of the tube 60 acts on the curved corners 56 and causes the corners 56 to be curled up and inward so that the member 18 is again folded lengthwise in the internal lumen 66 of the tube 60 as shown in FIG. 8B. The distal end of the heating member 18 may also include a cutout 57 which is shaped to accommodate the thicker portion of the papillary muscle 59 at the base of the chordae 14 during treatment of the chordae base, as shown in FIG. 8D.

The apparatus 10 also includes a shaft member 62 fixed to the proximal end of the heating member 18. The shaft member 62 is substantially disposed within the tube 60 and may include steering means at a proximal end configured for manipulation by a surgeon or other personnel performing the surgical procedure on the diseased tissue. In a preferred apparatus 10 for supplying thermal energy to a collagen based body structure, the shaft member 62 comprises a flexible, steerable catheter which includes a steering device (not shown) at the proximal end for bending and articulating the catheter during the surgical procedure. Steerable catheters such as described in U.S. Pat. No. 5,588,964 to Imran, et. al., incorporated herein by reference, are well known in the art and generally comprise one or more steering wires made of stainless steel or other high tensile wire, chord, or flat wire. The steering wires are fixed at a first end to the steering device disposed on the proximal end of the apparatus 10 and at a second end to the portion of the shaft member 62 which is desired to be manipulated. Tension is imparted to the steering wire by the steering device so as to cause the portion of the shaft member 62 to which the steering wire is fixed to curve in the direction of the steering wire. In this manner, the apparatus 10 may be manipulated in one or more directions to aid in the insertion and use of the device of the present invention.

FIG. 8D shows the apparatus in configured to apply thermal energy to the chordae surface of a diseased valve. A power supply chord 64 may be disposed within the wand member 62 which electrically connects a power source (not shown) with the one or more thermal heating elements a 34 disposed on the concave surface of the heating member 18. the power supply chord 64 may also include a control module (not shown) associated therewith which allows the operator to selectively control the intensity and duration of the thermal energy supplied to the collagen body structure.

The power supply chord 64 may also include an internal lumen or a separate lumen may be included which connects a vacuum port disposed on a treating surface of the heating member 18 with a vacuum supply source. The vacuum port (not shown) may configure to create a vacuum attachment with the collagen tissue to be treated. The ports enable the surgeon to more precisely administer thermal energy to the diseased collagen tissue of the heart valve. Alternatively, the vacuum port may be used to remove blood debris, electrolytic fluid, or other undesirable material from the area of interest.

It should be noted that although the described devices of FIGS. 4–8 are specially configured to effectively provide non-ablative thermal energy to the chordae of a diseased heart valve, specifically the mitral and tricuspid valves, the devices may also be used to apply thermal energy to a diseased annulus or a "billowing" or elongated leaflet.

Figure 9:
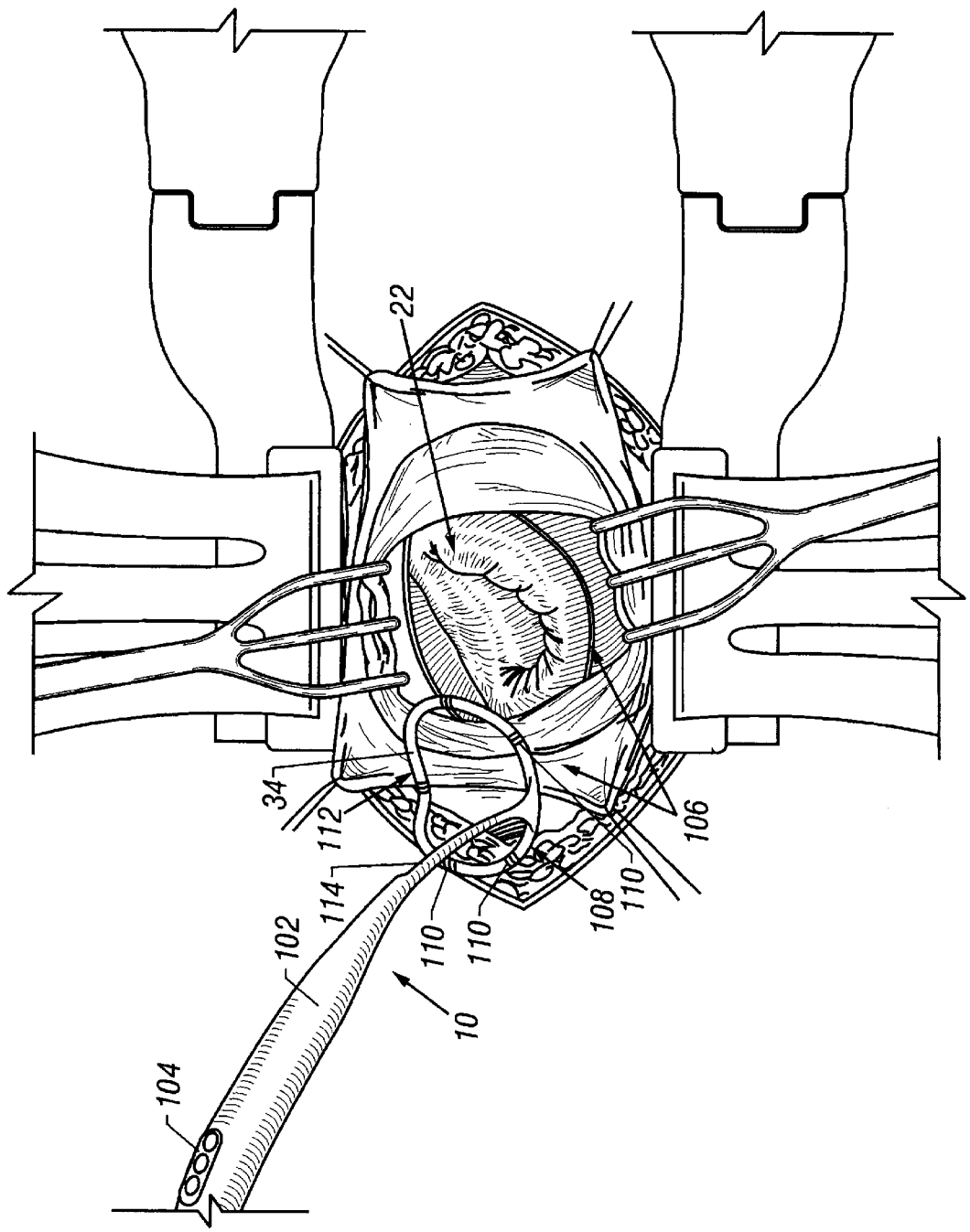
FIG. 9 shows a coronary procedure wherein an apparatus for supplying thermal energy to a collagen based body structure is used to remodel a diseased annulus of a mitral valve.
Figure 10:
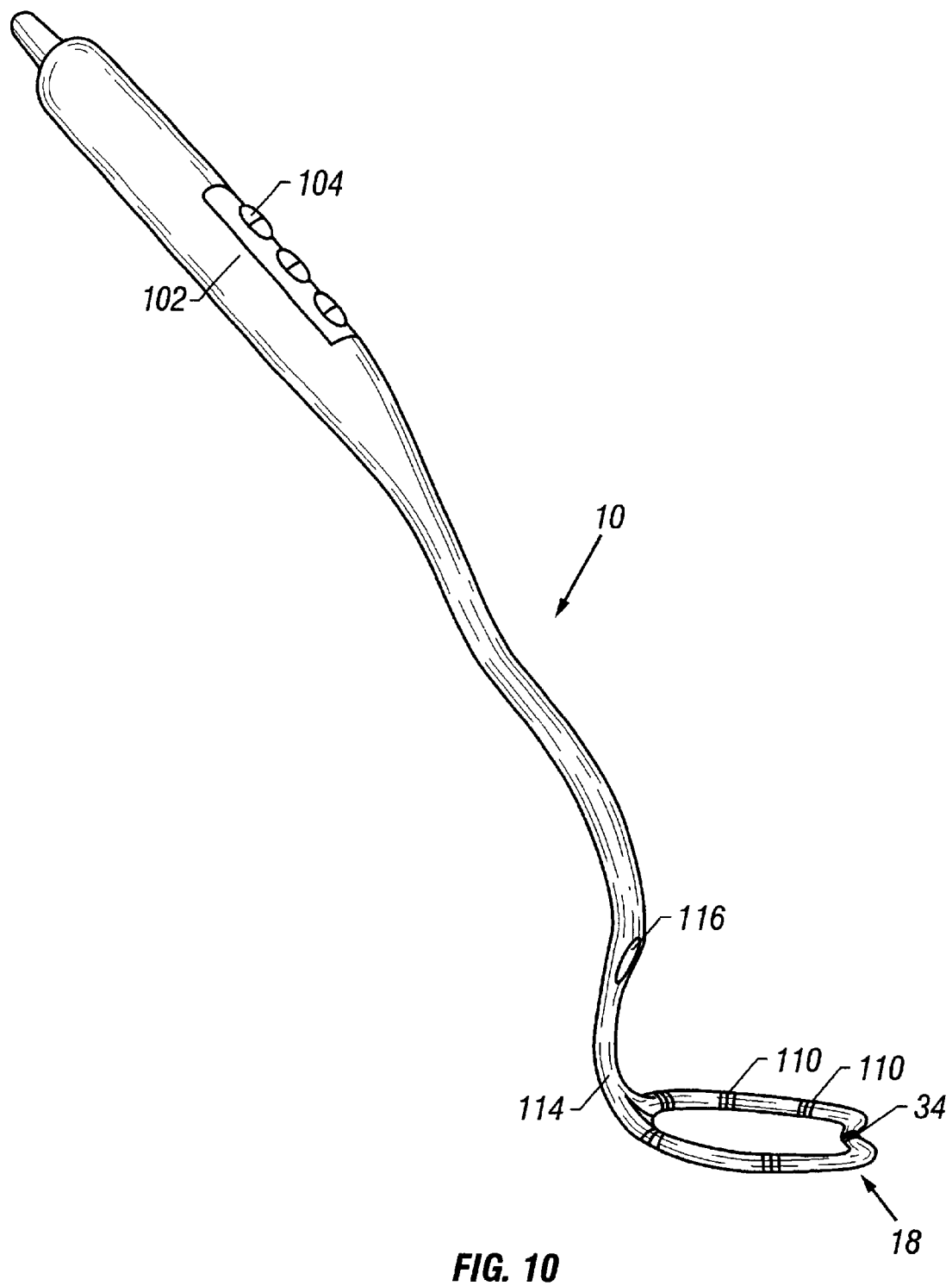
FIG. 10 is a perspective view of the apparatus of FIG. 9.

The teachings of the present invention also include specific devices and methods which are well suited for the repair and remodeling of the annulus and/or the leaflet of a diseased valve. FIGS. 9–10 illustrate an apparatus 10 for supplying thermal energy to a collagen based body structure wherein the apparatus is specially configured for applying thermal energy to a diseased annulus 106 of the mitral valve 22. The apparatus 10 comprises a handle portion 102 and a heating member 18 comprising a preferably ring-shaped annular configuration 108. The annular configuration 108 is fixed to a distal end of the handle portion 102 and is preferably configured from a conformable material which may be manipulated by the treating physician to allow the apparatus to be shaped to fit individual patient geometries and/or particular clinical applications. Located on the handle portion 102 are a number of controls 104 for controlling the duration and intensity of thermal energy supplied to the diseased annulus.

The annular configuration 108 is preferably configured to be substantially juxtaposed over the valve annulus 106 and has a circumference approximating that of the valve annulus 106, which is generally between 8.5–10 cm. Certain valvular diseases cause the annulus 106 to stretch due to a lack of oxygen, causing the normal "D"-structure of the annulus 106 to become more circular. The annular configuration 108 of FIG. 9 is configured to have a concave or recessed portion 112 so as to selectively shrink the collagen material of a diseased annulus 106 in order to restore the natural "D"-shaped geometry of the annulus 106. The heating member 18 includes a number of thermal elements or electrodes 34 placed around the periphery of the annular configuration 108 for selectively supplying thermal energy to the diseased annulus 106. It can be appreciated that although the apparatus 10 is specially configured for application of thermal energy to a diseased annulus 106, it may also be used to repair a billowing leaflet or an elongated chordae.

As shown in FIG. 10, the apparatus 10 may also include an endoscope 116 or other visualization device integrated into the handle portion 102. The endoscope 116 may include a fiber optic light bundle or other illumination means for illuminating the area of interest during the valve repair procedure. The apparatus 10 can thus be used to facilitate a minimally invasive, endoscopic, or percutaneous repair procedure wherein direct visualization of the area of interest would otherwise be difficult or impossible.

The device of FIG. 11 provides an alternate means of repairing a valve. particularly the annulus of the mitral valve, on a beating heart without interfering with the normal functioning of the heart. Here, apparatus 10 is configured to be percutaneously inserted and endovascularly delivered to the target heart valve. Apparatus 10 comprises an expandable basket member 120 disposed on a distal end of an insertion catheter 122. The expandable basket member 120 preferably comprises a distal ring 124, a proximal ring 125, and a medial ring 126, wherein the distal and proximal rings 124, 125 are sized to fit about a perfusion tube 130 slidingly disposed within the insertion catheter 122. The medial ring 126 is sized to contact an inner circumference of the diseased annulus. In a preferred configuration, the proximal ring 125 is fixed to the distal portion of the perfusion tube 130 with the distal ring 124 being slidably disposed about perfusion tube 130. Extending distally outward from the proximal ring 125 are a number of arms 136 which are fixed at a first end to the distal ring 124 and engage the medial ring 126 distal of the proximal ring 125. The arms continue distally from the medial ring 126 and bend inwardly to connect to the distal ring 124. The arms thus have a distal portion located distally of the medial ring 126 and a proximal portion located proximal of the medial ring 126.

The expandable basket member 120 shown in FIG. 11 is expanded by pushing the insertion catheter 122 distally relative to the perfusion tube 130, thus causing a reduction in the length L of the expandable basket member 120 and a concomitant increase in the diameter D of the medial ring 126 as the arms 136 are forced outward by the reduction in the length L. The medial ring 126 is preferably configured from a highly flexible material which tends to return to its original configuration when in a relaxed condition. For example, the medial ring 126 may be configured from NITINOL™, a flexible material well known in the art for use in similar applications. The arms 136 and distal 124 and proximal 125 rings may also be configured as a single unit comprising NITINOL™ or other suitable material so as to simplify construction and manufacture of the basket 120. The apparatus 10 is contracted by extending the perfusion tube 130 distally relative to the insertion catheter 122. This causes an increase in the length L of the expandable basket member 120 and a concomitant decrease in the diameter D of the medial ring 126.

In an alternative configuration of the expandable basket 120, the device may be configured to be disposed within the insertion catheter 122 in a contracted state during insertion and removal of the apparatus 10. In such a configuration, the internally disposed perfusion tube 130 is slidable relative to the insertion catheter 122. The distal ring 124 is preferably slidable relative to the perfusion tube while the proximal rind 125 is fixed to the perfusion tube. The arms 136 are configured to spring outwardly from the perfusion tube when the device is in an "open" position. In a "closed" position, the insertion catheter 122 is advanced distally relative the perfusion tube 130. The distal edge 123 of the catheter 122 first contacts the arms 136 proximate the proximal ring 125 and causes the arms to be forced inward to lay in close proximity with an outer surface of the perfusion tube 130. The resultant reduction in the diameter D of the basket 120 causes a concomitant increase in the length L of the basket 120 and the distal ring 124 is slid distally.

Figure 11B:
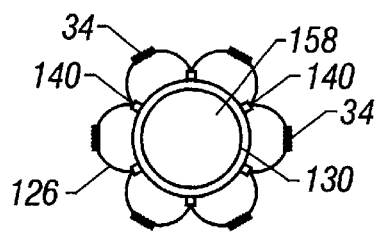
FIGS. 11(A–D) illustrate an apparatus for supplying thermal energy to a collagen based body structure which is configured to repair a diseased valve without interfering with the cardiac function of the heart.
Figure 11A:
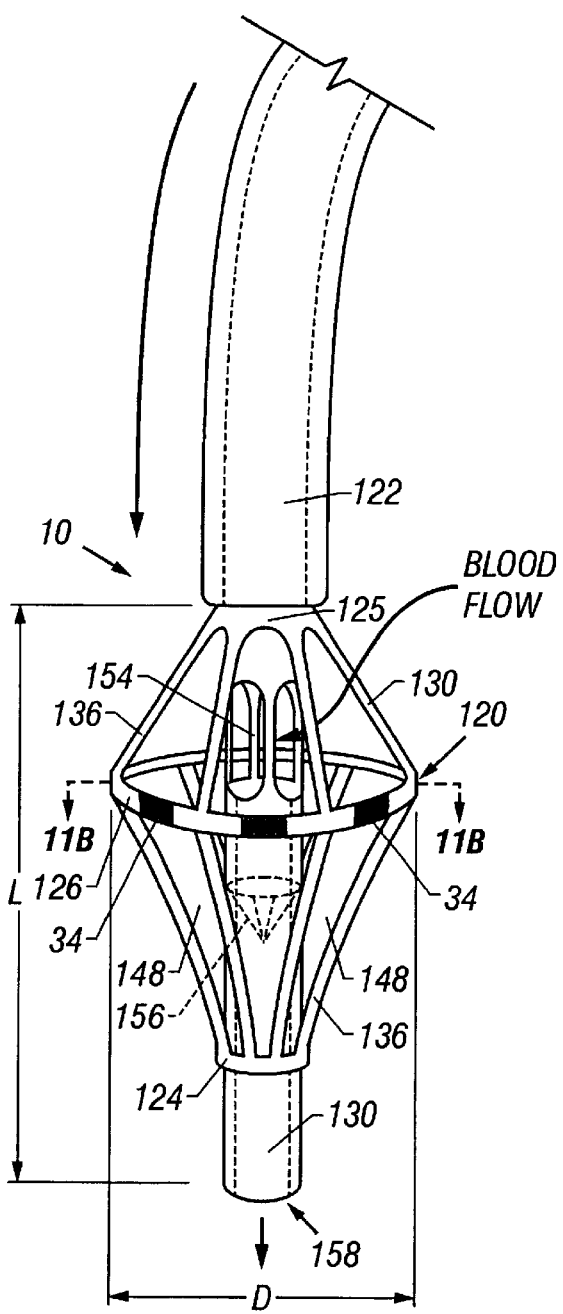

The insertion catheter 122 is advanced distally relative to the basket 120 and the perfusion tube 130 until the basket is completely disposed within an inner lumen 127 of the catheter 122. The distal edge 123 of the insertion catheter 122 is preferably configured as shown in FIG. 11D to have an atraumatic outer edge to prevent damage to surrounding body tissue during insertion of the device and may also include a shaped inner edge portion for gently urging the flexible arms 136 inward during contraction of the basket within the inner lumen 127.

In an "open" state, the outer diameter of the medial ring 126 may be controlled by selectively advancing or withdrawing the perfusion tube 130 relative to the insertion catheter 122. In this manner, the arms 136 are forced closed or are allowed to expand relative to the perfusion tube 130, causing the diameter D of the medial ring 126 to be varied. A number of configurations are possible for making the diameter of the medial ring 126 variable. One such configuration is shown in FIG. 11B wherein the cross section taken along line 11B—11B in FIG. 11A of a completely contracted expandable basket member 120 is shown. The medial ring 126 is configured having a number of flex points 140 at the points of engagement with the arms 136. These flex points cause the medial ring 126 to contract about the perfusion tube 130 to form to a configuration as shown in FIG. 11B.

Figure 11C:
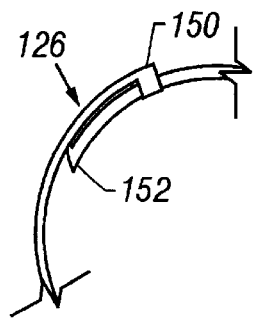
Figure 11D:
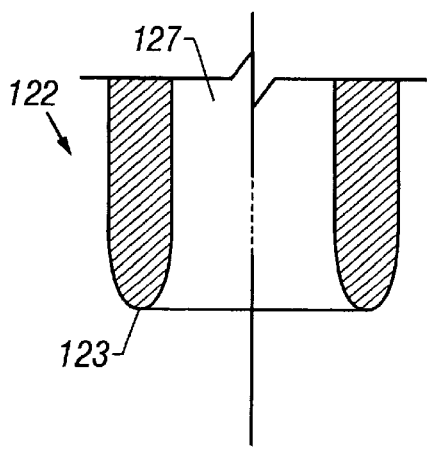

Another expandable ring configurations is shown in the cut-away cross-section of FIG. 11C wherein the ring 126 is slidably engaged to itself. In a fully expanded condition, an engagement means 150 at a first end of the medial ring engages a stop means 152 at a second end of the ring 126. When the medial ring 126 is in a contracted position, the engagement means 150 slides circumferentially apart from the stop means 152 thus decreasing the circumference of the medial ring 126. The medial ring 126 may also be configured from a highly flexible cable which easily collapses on itself when contracted and readily expands with the movement of the perfusion tube 130 relative to the insertion catheter 122. Regardless of the chosen configuration, the medial rind 126 includes a number of heating elements 34 which are configured to contact a diseased annulus and selectively contract the collagen of the annulus using non-ablative thermal energy. A preferred apparatus of the present invention includes one or more heating elements disposed on the arms 136 adapted to provide thermal energy to the leaflets of the treated valve as well as the valve annulus.

The arms 136 may be fixed at an engagement point on the medial ring 126 or the arms 136 may be movable relative to the circumference of the medial ring 126. In an alternate configuration, the distal 124 and/or proximal 125 rings may be omitted entirely with the arms 136 being fastened directly to the insertion catheter 122 at the proximal end of the arms 136 and to the perfusion tube 130 at the second end of the arms 136 or in an alternate configuration fixed to the perfusion tube 130 at one end and slidingly fixed to the perfusion tube 130 at a second end.

A method of use of a device of the present invention shown in FIG. 11 comprises providing a working space proximate the diseased heart valve. The surgeon may use any of a number of well know access procedures for gaining access to the pericardial cavity and providing a working space proximate the valve to be treated. An apparatus 10 for supplying thermal energy to a collagen based body structure is advanced into the area of interest proximate the diseased valve, the device maintained in a closed configuration wherein the distal ring 124 is separated to the maximum extent relative to the proximal ring 125. The collapsed basket member 120 is thus easily insertable through a small incision and may be advanced endovascularly without substantial difficulty.

Once in place proximate the diseased heart valve the basket member 120 may be expanded by pushing the perfusion tube 130 distally relative to the insertion catheter 122. The size of the medial ring 126 may be adjusted by varying the degree to which the distal ring 124 and proximal ring 125 are separated relative to each other. The apparatus may be used for a variety of annuli geometries by intraoperative adjustment of the external circumference of the basket member 120.

For treatment of a diseased annulus, the basket member 120 of the apparatus 10 is advanced to a point where the medial ring 126 is juxtaposed against the circumference of the annulus to be treated. The surgeon then selectively provides energy to one or more thermal heating elements 34 circumferentially disposed about the medial ring 126. Thermal heat is selectively supplied to the tissue of the annulus so as to selectively contract the annulus to a position more closely approximating the size and geometry of a healthy valve annulus.

The apparatus 10 for supplying thermal energy to a collagen based body structure may also include a membrane 148 stretching between the distal portions of the arms 136. The membrane 148 prevents blood from flowing retrogradely from the left ventricle into the atrium during the surgical repair procedure on the mitral valve 22. Flow of blood from the atrium to the ventricle is accomplished through a number of perfusion ports 154 cut in the wall of the perfusion tube 130 wherein the ports 154 are in fluid communication with a perfusion lumen 158 formed within the perfusion tube 130. When the apparatus is properly positioned within the heart chamber, the perfusion ports 154 are situated within the left atrium and the perfusion lumen 158 empties into the left ventricle. The blood is thus shunted from the left ventricle through the perfusion lumen 158 into the chamber of the left ventricle during a repair procedure on the mitral valve.

Figure 12A:
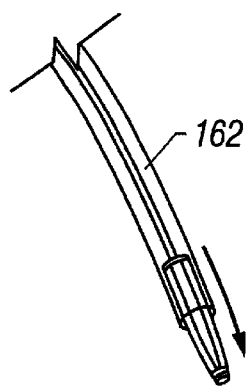
FIGS. 12(A–C) illustrate an alternative configuration of an apparatus for supplying thermal energy to a collagen based body structure in use to repair diseased annuli and leaflets.
Figure 12B:
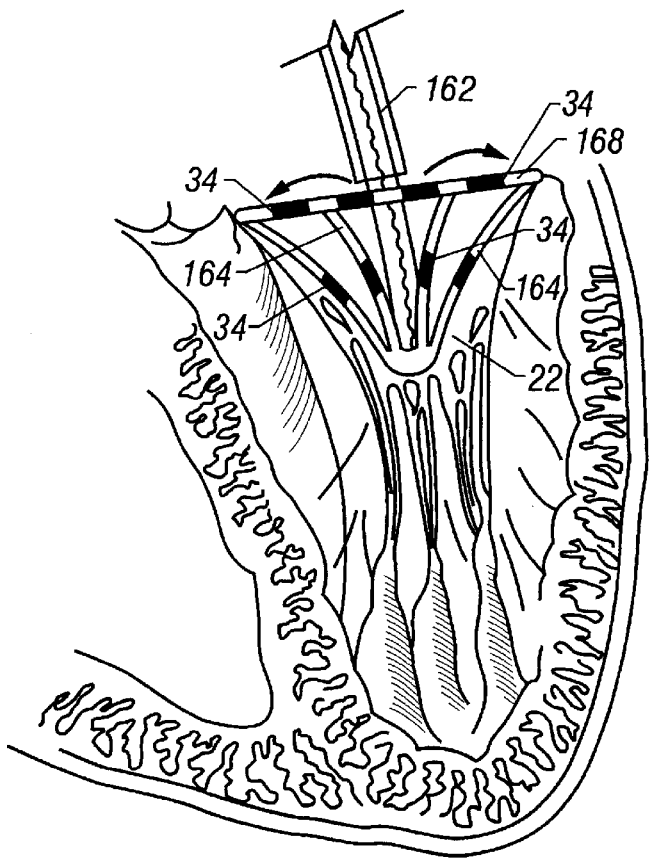
Figure 12C:
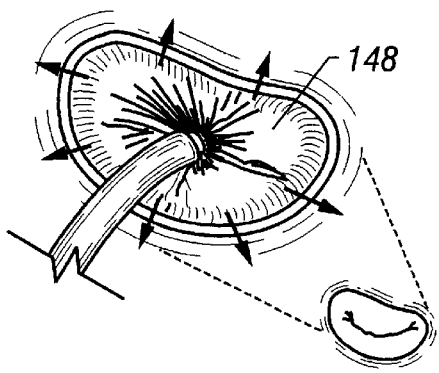
Figure 13A:
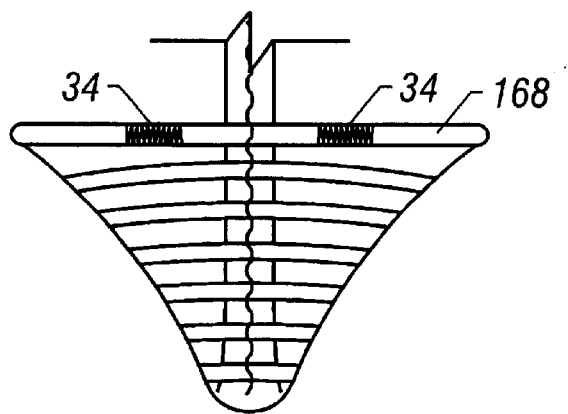
FIGS. 13(A–C) illustrate alternative configurations of an apparatus for supplying thermal energy to a collagen based body structure which are configured to repair a diseased annulus.
Figure 13B:
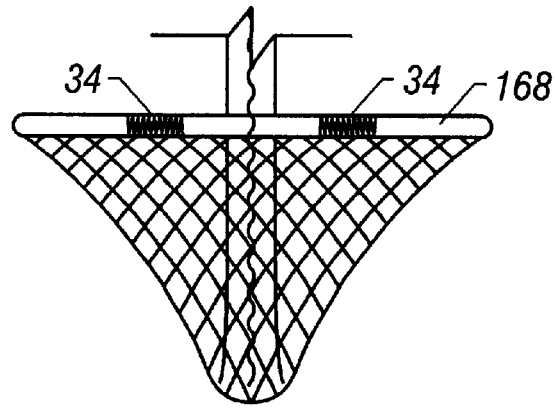

The perfusion lumen 158 preferably includes a valve 156 such as a duckbill valve which prevents flow from the ventricle back into the left atrium during the pumping cycle of the left ventricle. The apparatus 10 thus functions as normally would the heart valve during the repair procedure so that the repair on the valve may be accomplished without stopping the heart. Alternatively, the membrane 148 may seal the region between an outer circumference of the perfusion tube 130 and the circumference of the medial ring 126. In any event, located upstream of the membrane 148 is one or more perfusion ports 154 which allow blood to flow normally through the perfusion lumen 158 in the normal direction of blood flow. The configuration can be reversed for alternative access procedures or orientations of the basket member 120 in the chambers of the heart to allow for blood flow in the opposite direction if required FIGS. 12–13 show a number of alternate configurations of an apparatus 10 for supplying thermal energy to a collagen based body structure which are particularly suited for repairing a diseased annulus or leaflet. FIG. 12A shows an umbrella type apparatus 10 for supplying thermal energy to a collagen based body structure wherein the apparatus is disposed within a trocar insertion sleeve 162. The apparatus 10 includes an umbrella member 160 comprising a number of arms 164 each having a distal end and a proximal end wherein the proximal distal of the arms 164 are fixed to a distal end of an elongate member 30. When disposed within the trocar insertion sleeve 162 the arms 164 extend proximally from the distal end of the elongate member 30. Distal movement of the elongate member 30 relative to the sleeve 162 causes the arms 164 to spring outwardly from the elongate member 30 when the arms 164 are free of the restraining force insertion sleeve 162.

The maximum expansion of the arms 164 may be controlled by a ring 168 to which the proximal ends of the arms 164 arc circumferentially fixed. The ring 168 is preferably a flexible cable which allows it to be easily disposed within a relatively small diameter trocar insertion sleeve 162. The ring 168 and arms 164 include a plurality of heating elements 34 for supplying thermal energy to the annulus 106 and/or the leaflets or chordae of the diseased valve. The umbrella member 160 may also include a membrane 148 sealing the space defined within the ring 168. As shown in FIG. 12C, the membrane 148 seals the valve to be treated against blood flow during performance of a valve repair procedure.

Figure 13C:
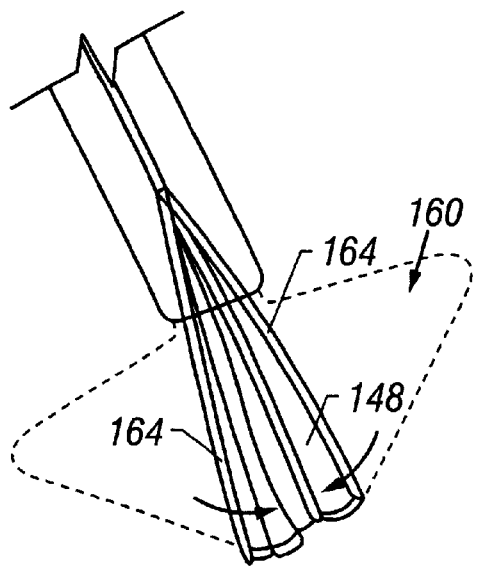

A variety of shapes and configurations are possible for the umbrella member 160. FIGS. 13(A–C) show several configurations which are possible with the teachings of the present invention for an apparatus for supplying thermal energy to a collagen based body structure. FIG. 13C shows one means of allowing endoscopic removal of the umbrella member 168 from the area of interest using a trocar insertion sleeve 162. Retraction of the umbrella member 160 and the elongate member 30 within the trocar insertion sleeve 162 causes the distal end of the trocar insertion sleeve 162 to press against the arms 164 and fold the flexible arms 164 over distally so that the umbrella member 160 may be withdrawn into the sleeve 162.

The teachings of the present invention also include methods for repair of a diseased heart valve using thermal energy. A method of use of the present invention comprises a first step of providing a working space proximate the area of interest: the diseased heart valve. Physician access to the exterior surface of the heart may be achieved by several conventional cardiac access procedures which have been developed for traditional heart valve surgery such as by a median sternotomy or a thoracotomy. Access to the target heart valve can also be provided via a minimally invasive surgical techniques, such as a mini-sternotomy,or a mini-thoracotomy; endoscopically through a small trocar port or incision; or percutaneously through a major vein (e.g. femoral vein, vena cava) or artery (e.g. femoral artery, subclavian artery aorta, etc.). Access may also be provided using a sub-xyphoid or xyphoid approach as described in U.S. patent application Ser. No. 09/071,757, incorporated herein by reference in its entirety.

The method and location for access to the heart will largely depend on the valve to be treated, the particular patient anatomy, and surgeon preference. For example, in a direct surgical approach, the aortic valve may be reached via a sternotomy or mini-sternotomy using a "J"- or "T"-incision at the $3^{rd}$, $4^{th}$, or $5^{th}$ intercostal space. A right thoracotomy or right mini-thoracotomy as well as a full sternotomy are suited for providing access to the mitral valve. For access to the tricuspid or the pulmonic valve, the surgeon may use a minimally invasive mini-sternotomy on the $3^{rd}$, $4^{th}$, or $5^{th}$ intercostal space or a left mini-thoracotomy or left thoracotomy.

Figure 14:
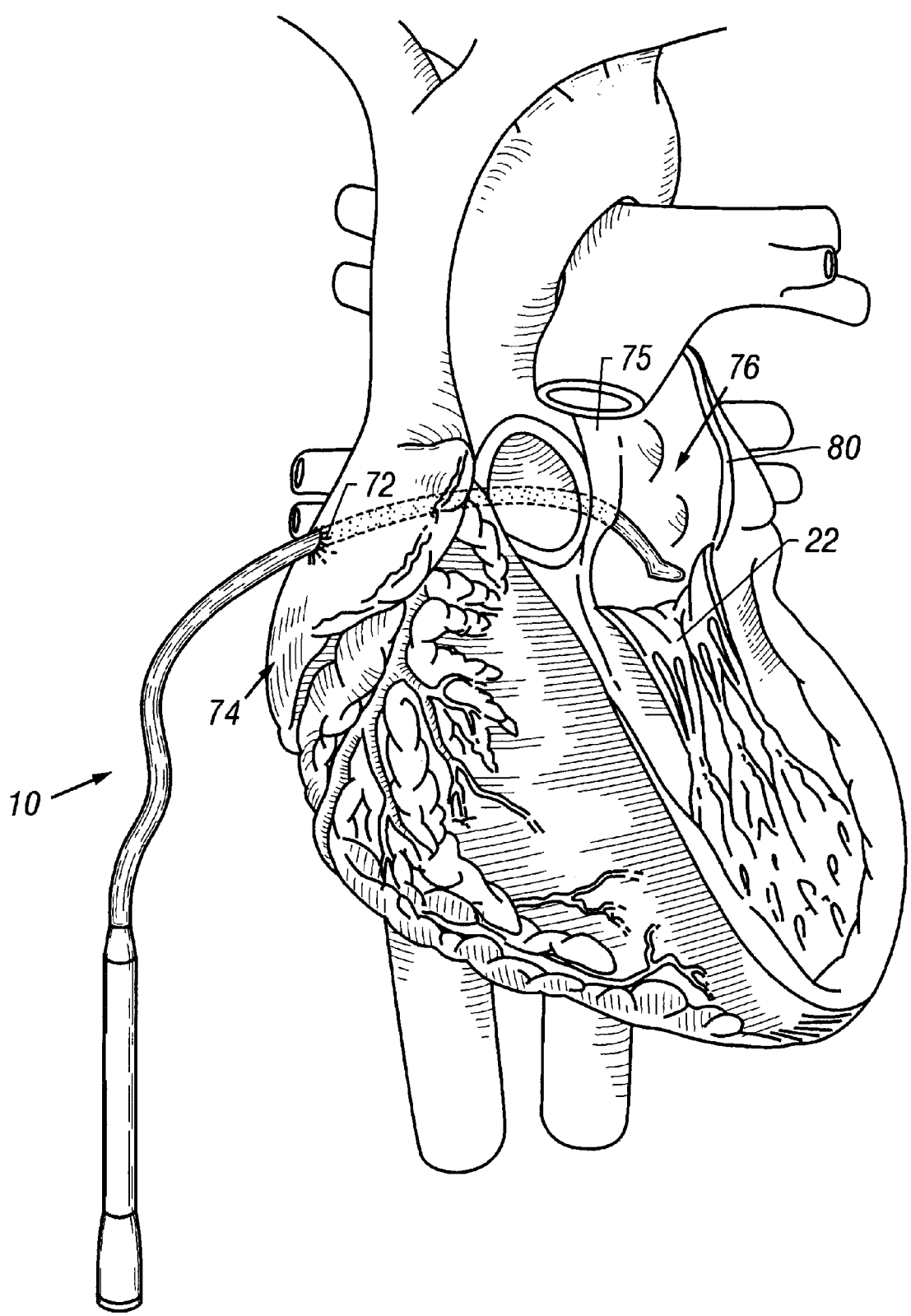
FIG. 14 illustrates a method of accessing a diseased mitral valve with an apparatus for supplying thermal energy to a collagen based body structure.

FIG. 14 illustrates the use of an apparatus 10 of the present invention such as that of FIG. 5, to repair the mitral valve of a patient, wherein the apparatus is shown accessing the interior chambers of the heart. The exterior surface of the heart is first accessed using a direct surgical approach (sternotomy, thoracotomy, minimally invasive access, sub-xyphoid, etc.). Although the following description is specifically directed to access of the mitral valve of the patient, it should be understood that the examples herein are demonstrative and that simple modifications to the above procedures are well known in the art for accessing and repairing the other valves of the heart.

As shown in FIG. 14, once the heart surface has been sufficiently exposed, the apparatus 10 is inserted through an incision 72 made in the wall of the right atrium 74 and through the septal wall 75 separating the right 74 and left 76 atrium. Once in the left atrium 76, the mitral valve 22 is treated according to the teachings of the present invention. A transeptal approach to the mitral valve 22 from the right atrium 74 is well known in the art and is often the most desirable means of accessing the mitral valve 22 as it prevents damage to the nerves of the left atrial wall 80. The angle of the mitral valve 22 within the left atrium 76 may also make this a more desirable means of accessing the diseased valve 22.

Figure 15:
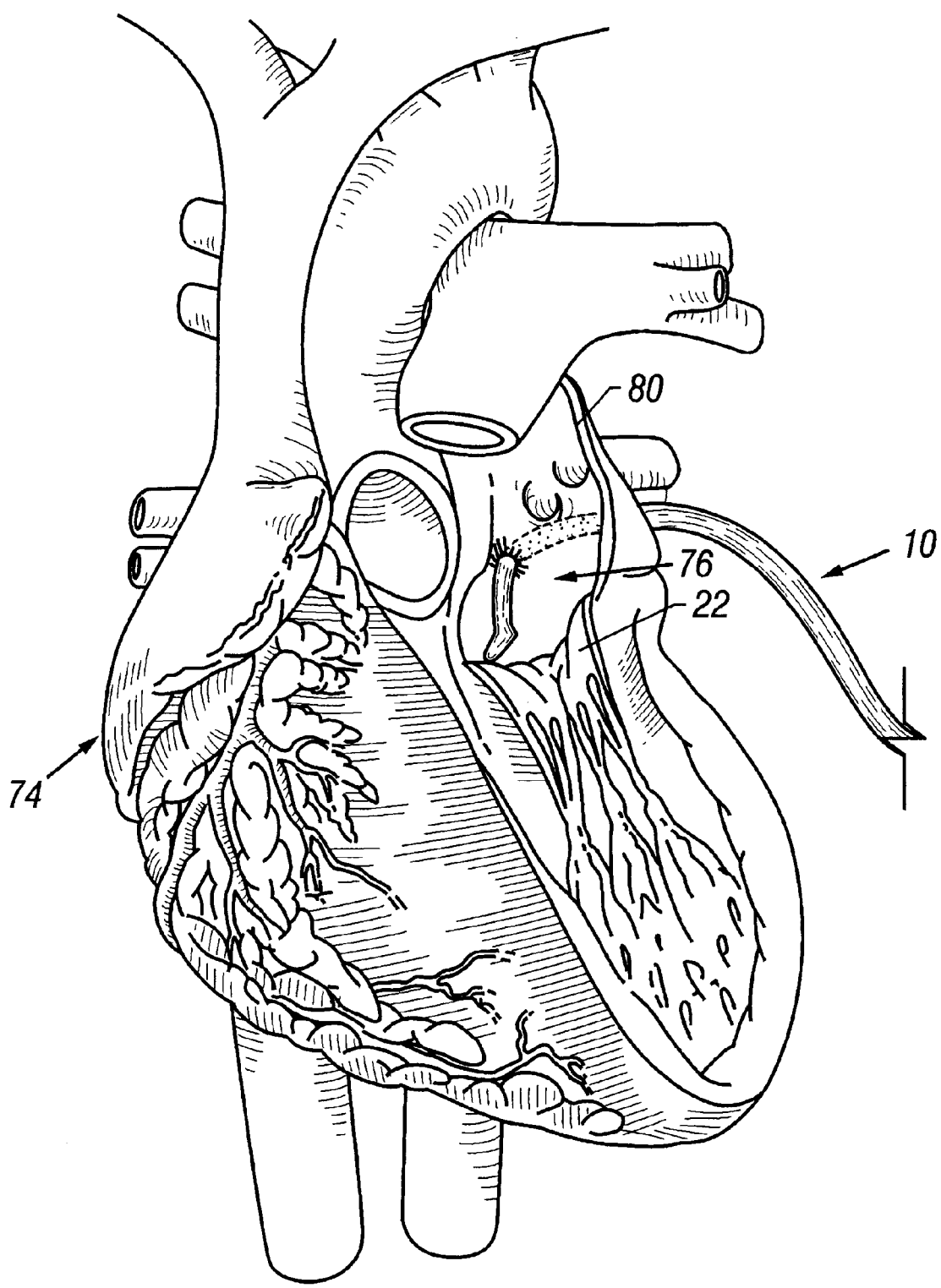
FIG. 15 illustrates a method of accessing a diseased mitral valve with an apparatus for supplying thermal energy to a collagen based body structure.

FIG. 15 shows an access method for providing a working space proximate the mitral valve 22 wherein an apparatus 10 is inserted directly through the atrial wall 80 of the left atrium 76. This method may be preferred as it does not require making an access incision in the septal wall 75 to provide access to the left atrium 76. However, the wall of the left atrium 76 may be an undesirable site for accessing the mitral valve 22 because of the large number of nerves in the left atrium 76 and the possibility of adversely affecting cardiac functioning by damaging the atrial muscle or the atrial nerves. As shown in FIG. 15, access through the left atrium 76 may require the apparatus 10 to sharply bend proximate the distal end in order to effectively treat the mitral valve 22. Bending the apparatus 10 in this fashion may increase the difficulty of the procedure or require that the apparatus 10 be made steerable to allow the operator to manipulate the heating member 18 during installation and treatment.

Figure 16:
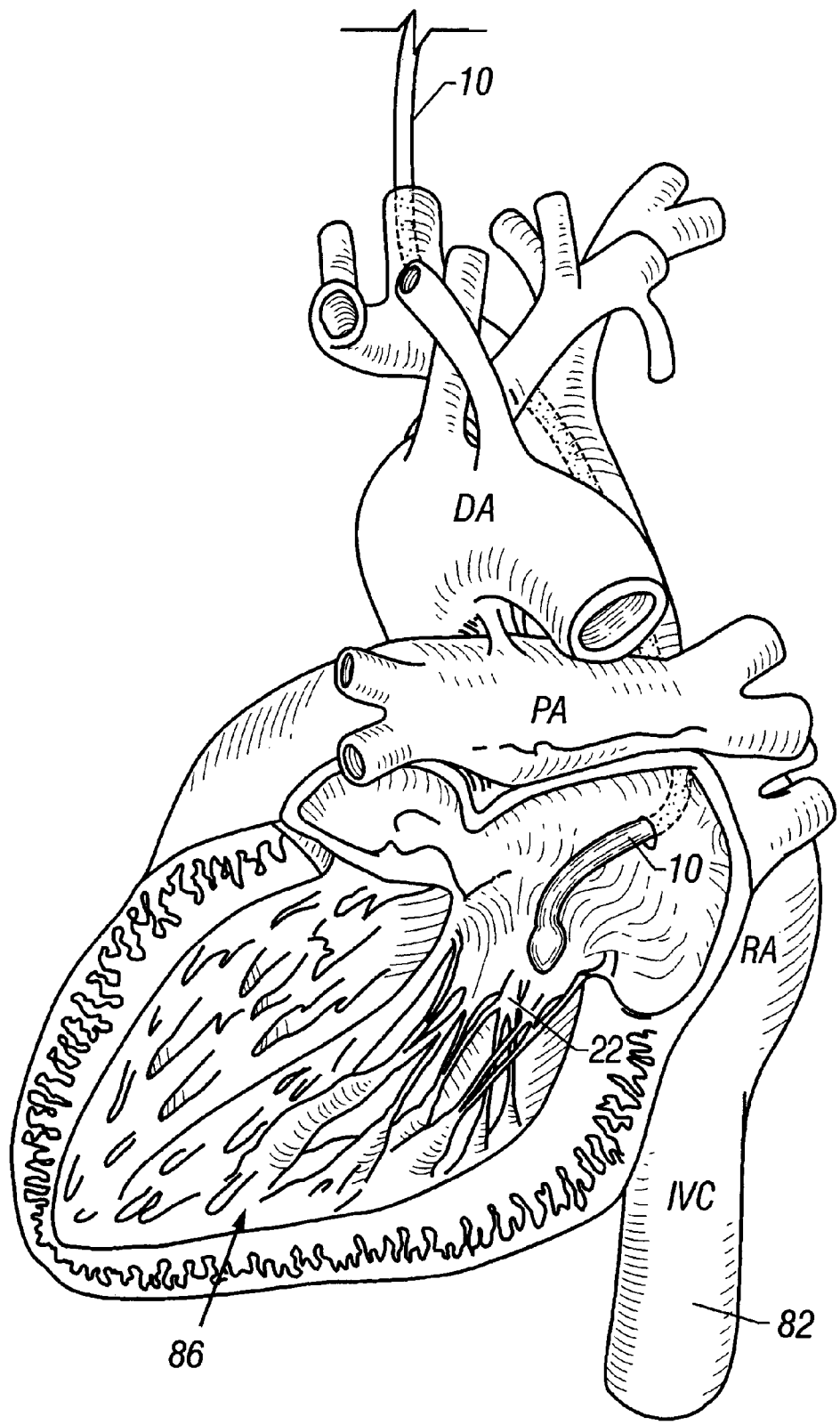
FIG. 16 illustrates a method of accessing a diseased mitral valve with an apparatus for supplying thermal energy to a collagen based body structure.

The need for access procedures to the surface of the heart may be avoided by the use of an endovascular access procedures. Generally, an endovascular access procedure is accomplished by inserting a catheter device through a percutaneous or "direct cut-down" incision into a major vein or artery of the patient and then threading the catheter along the vessel pathway to an interior portion of the heart. FIG. 16 shows one method of accessing the mitral valve 22 of a patient wherein the apparatus 10 is inserted into the patient's vasculature percutaneously and advanced to the interior chamber of the heat endovascularly. Specifically, the apparatus 10 is inserted into the left internal jugular (not shown) of the patient and advanced to the right atrium 74. The apparatus 10 is then, after a transeptal pierce, advanced transeptally from the right atrium 74 to the left atrium 76 to the mitral valve 22.

Figure 17:
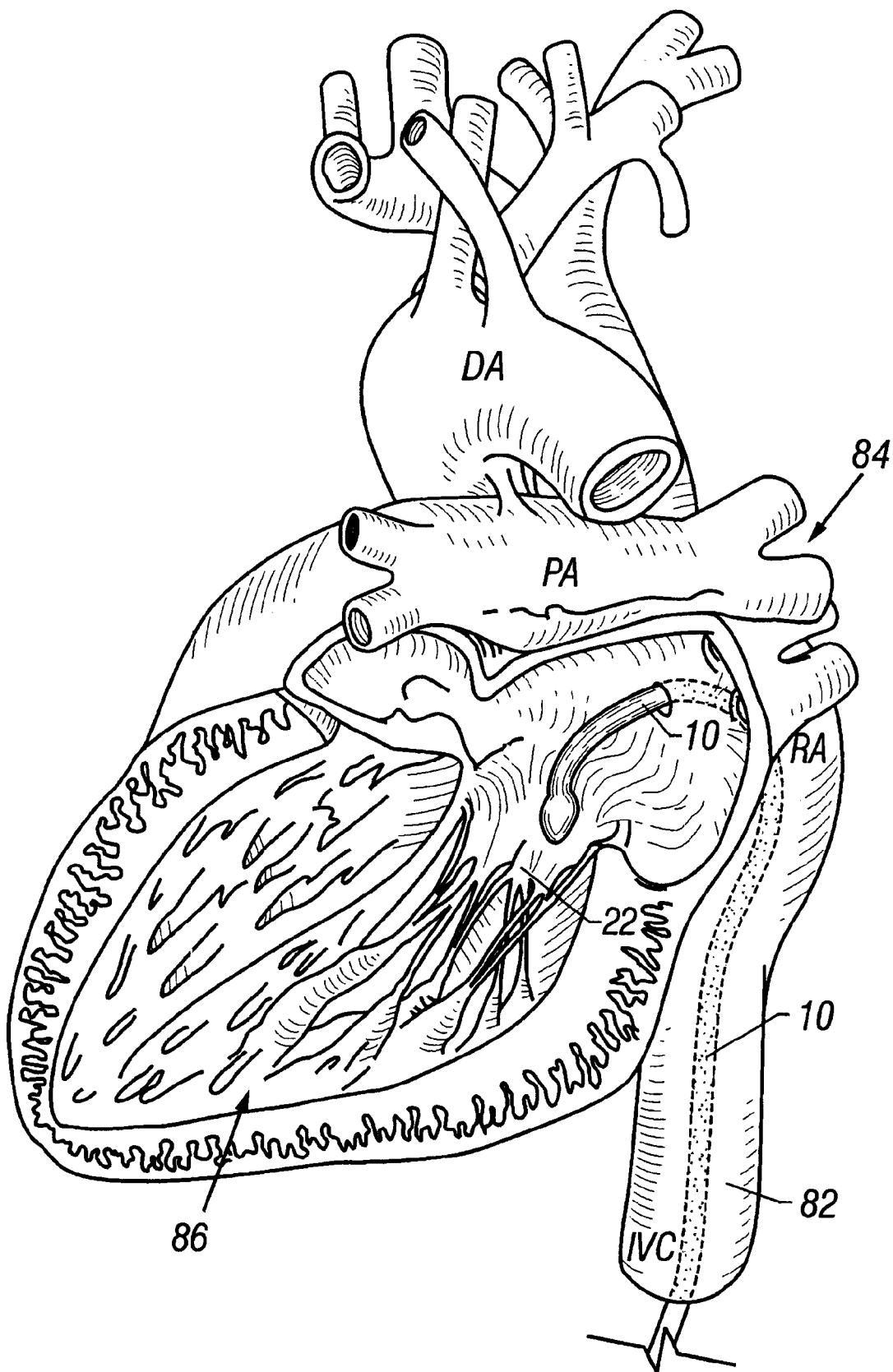
FIG. 17 illustrates a method of accessing a diseased mitral valve with an apparatus for supplying thermal energy to a collagen based body structure.
Figure 18:
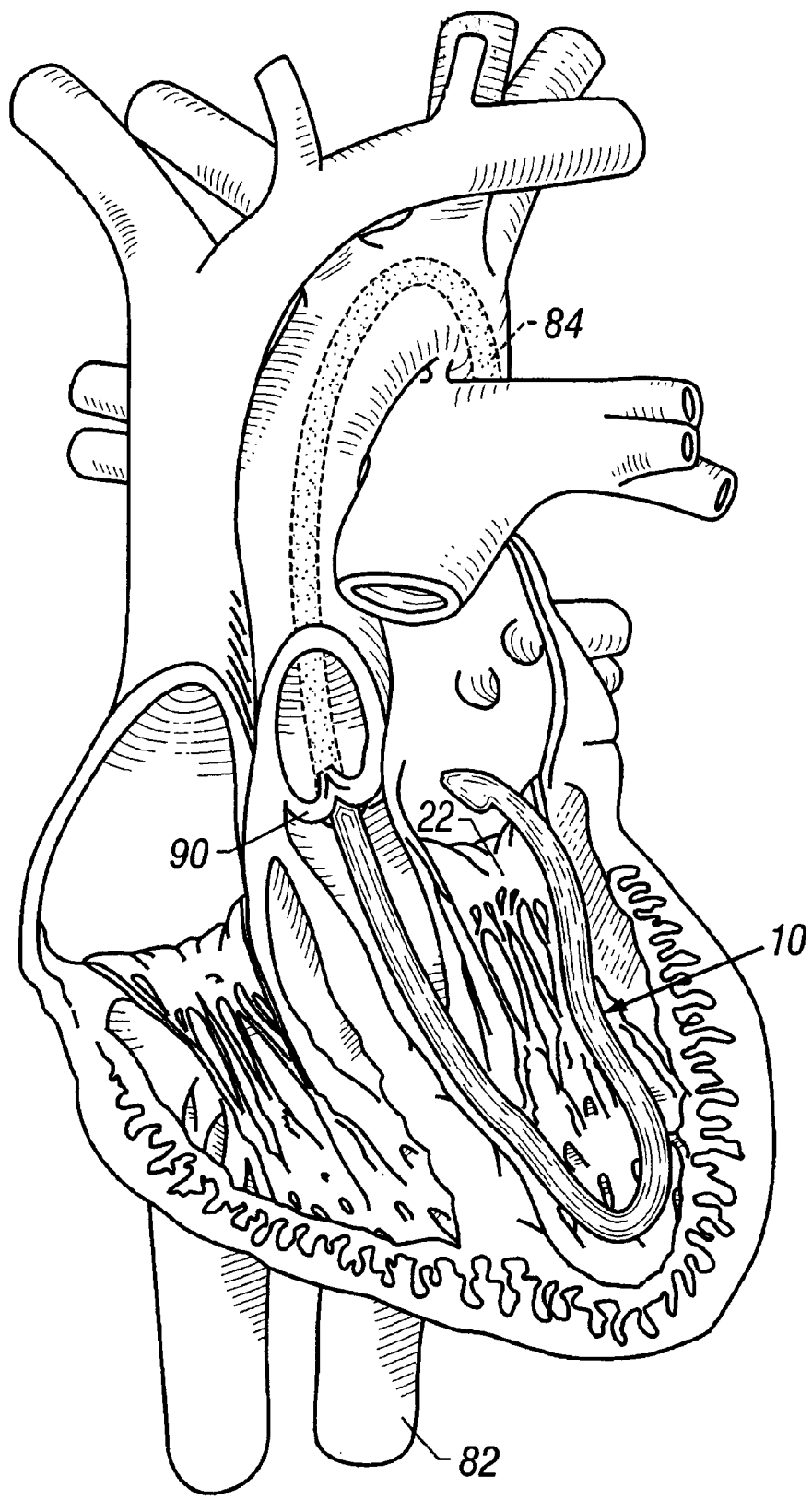
FIG. 18 illustrates a method of accessing, a diseased mitral valve with an apparatus for supplying thermal energy to a collagen based body structure.

FIG. 17 shows another percutaneous/endovascular access procedure whereby the apparatus 10 is inserted into the femoral vein (not shown) to the inferior vena cava 82 and then into the right atrium 74. From there, the apparatus 10 transeptally accesses the left atrium 76 and the mitral valve 22. In FIG. 18, the apparatus 10 is inserted via the femoral artery, (not shown) around the aortic arch 84, across the aortic valve 90 and into the left ventricle 86. The method of FIG. 18 may also require the use of a steerable apparatus to navigate the sharp bends required. In generals the advantage of a percutaneous incision and an endovascular approach like those illustrated in FIGS. 16–18 is that the necessity for a major incision or surgical wound is eliminated. A percutaneous/enidovascular procedure may also be performed on a beating heart which eliminates the complications and patient trauma of a cardiopulmonary bypass (CPB) procedure.

Once a suitable access space has been provided proximate the mitral valve and an apparatus of the present invention is in place, the next step in a method of the present invention is to contact the diseased portion of the vessel with the thermal heating element of a device of the present invention.

Treatment sites may include a diseased chordae, a billowing leaflet, or a misshapen annulus. For a diseased chordae, a thermal heating element of a device of the present invention contacts the chordae and thermal energy is supplied to the chordae so as to selectively shrink the chordae. For a billowing leaflet, thermal energy is supplied to the leaflet directly or to the attached chordae to eliminate the excess tissue of the diseased portion. Treatment of a diseased annulus may be accomplished by selective contact of at least a portion of the annulus with a thermal heating member so as to restore the proper size and "D"-shaped configuration of the annulus.

One advantage of the present invention is that the valve repair procedure may be accomplished either on a beating heart or on a non-beating heart placed on cardiopulmonary bypass and cardioplegic arrest. The heart may also be partially assisted as more fully discussed in copending U.S. patent application Ser. No. 09/118,132 incorporated herein by reference in its entirety. When the procedure is performed on a beating heart or partially assisted beating heart, a method of the present invention includes the additional step of monitoring the valve function with a monitoring device simultaneously with thermally treating the diseased valve structure. Monitoring valve function simultaneously with treatment of the diseased valve allows the surgeon to receive real time feedback as to the treatment results. The surgeon can continue to provide thermal treatment to the valve structure based on the clinical indications received via the real time monitoring of the functioning of the valve. When the monitoring feedback indicates optimum performance from the repaired valve, the surgeon can then terminate thermal treatment of the valve.

A monitoring device suited for use with the method of the present invention is a transesophegial echocardiography (TEE) apparatus inserted as is known in the art in the esophagus of the patient to image the heart. The TEE catheter can be used to provide real time feedback on valve performance without interfering with the cardiac procedure. Installation of an apparatus of the present invention and manipulation of the apparatus during treatment may be extremely difficult for most access techniques, requiring the use of an imaging apparatus of some sort. A number of imaging devices and techniques are appropriate for use with the apparatus of the present invention. As mentioned earlier, visual guidance may be provided using an endoscope. Endoscopic visualization may be accomplished using either an endoscope integrated into the construction of an apparatus of the present invention or an endoscope may be separately installed to image the area of interest.

In addition to endoscopic visualization, other visualization techniques are suitable for aiding in the installation and manipulation of the apparatus within the heart, including techniques such as transesophegial echocardiography (TEE), intracardiac ultrasound (IVUS), transthoracic echocardiography, infrared (IR) imaging, and traditional fluoroscopic radiography techniques. To aid in visualization and identification of the apparatus, the apparatus may be constructed from radio-opaque materials or one or more radio-opaque marker elements may be placed on the apparatus.

Figure 19:
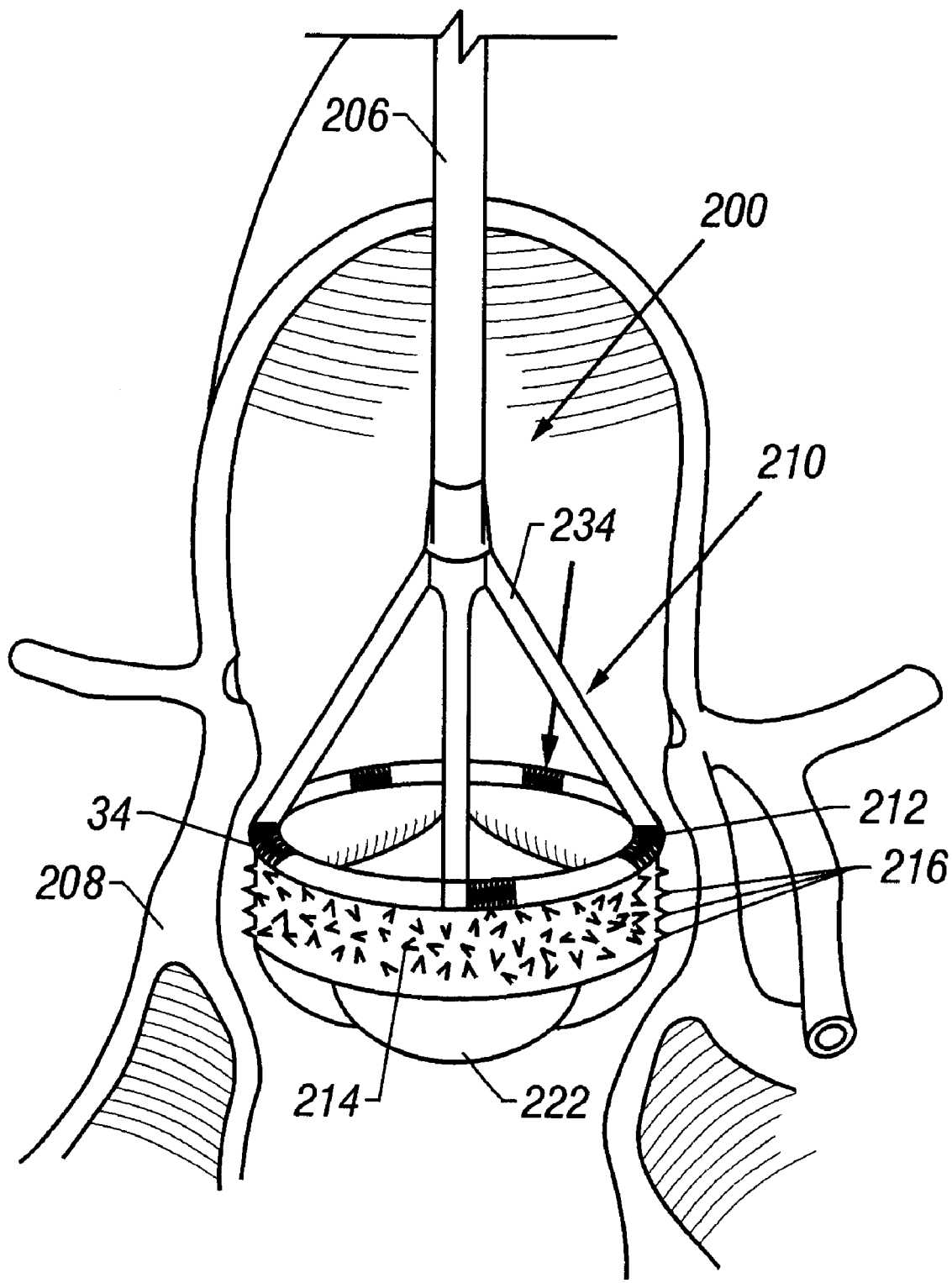
FIG. 19 shows a thermal valve replacement device replacing a diseased aortic valve with a prosthetic replacement valve.

The teachings of the present invention include devices suited for the replacement of a diseased valve with a replacement valve. A device for supplying thermal energy to a collagen based body structure can be utilized in a valve repair procedure to install and fix the replacement valve within the annulus of the diseased valve. FIG. 19 shows a thermal valve replacement device 200 of the present invention wherein the device 200 comprises a valve holder 210 fixed to the distal end of an insertion member 206. The device 200 is configured to replace a diseased aortic valve with a prosthetic valve 222 wherein the diseased valve has been removed leaving only the valve annulus 208.

The valve holder 210 of the present invention may include a heating ring 212 for supplying thermal energy to a collagen based body structure wherein the heating ring 212 is specially configured for treatment of the annulus 208 of a diseased valve. The valve holder 210 securely holds the replacement valve 222 while supplying thermal energy to the tissue of the annulus 208 surrounding the replacement valve 222 through the heating ring, 212. In this manner, the collagen tissue of the annulus 208 is contracted about the replacement valve 222. effectively fixing the replacement valve 222 in the annulus 208 without the need for suturing, stapling, or performing other difficult manual surgical fixation procedures.

Figure 20:
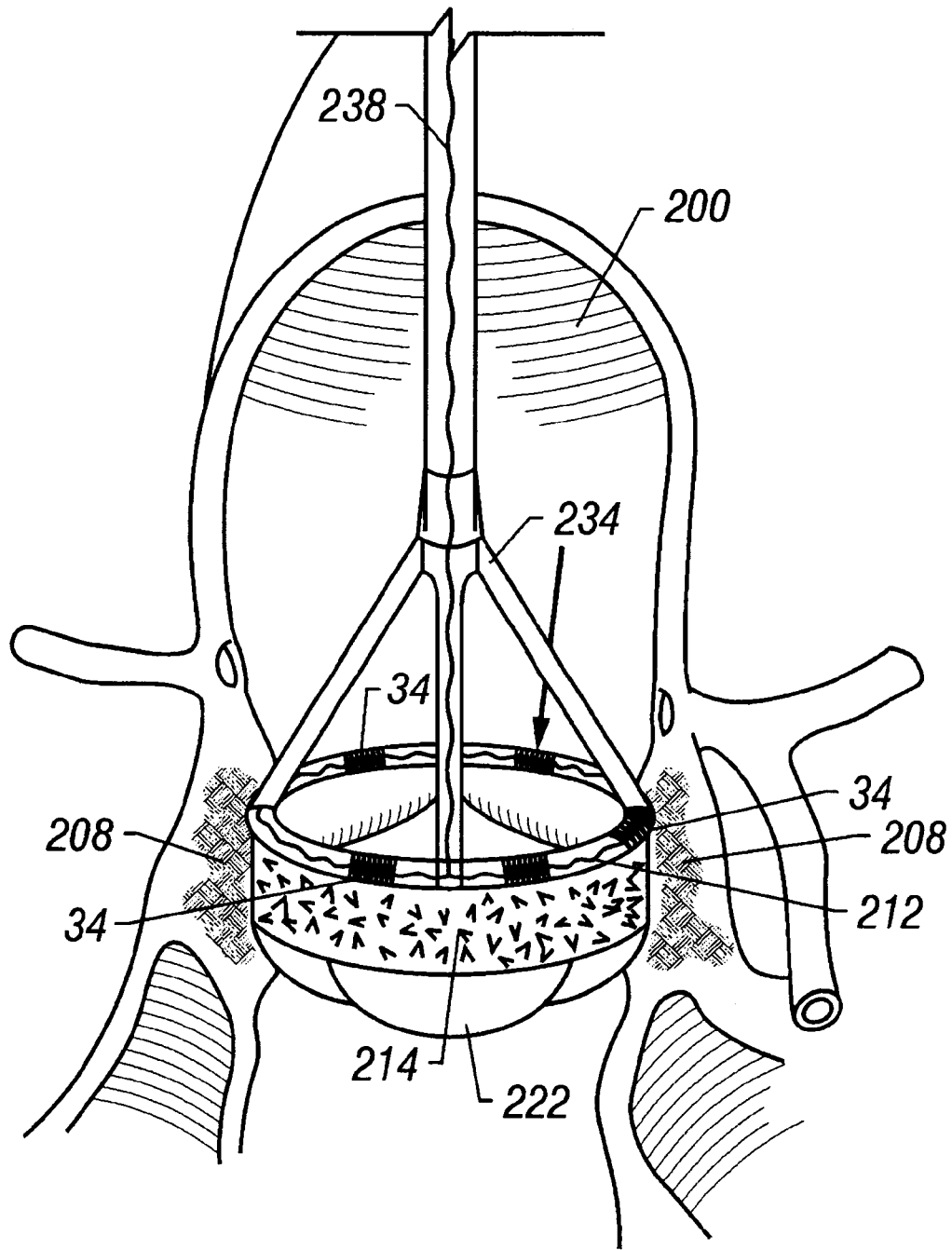
FIG. 20 shows the thermal valve replacement device of FIG. 19 holding a replacement valve in place within the annulus where the annulus of the diseased valve is contracting around the replacement valve following the application of thermal energy to the annulus.

A preferred replacement valve 222 is illustrated in FIG. 22A. The heart valve 222 includes a collar portion 214 having a plurality of spines 216 which are configured to engage the wall of the annulus 208 when the annulus 208 is contracted about the valve 222. The spines 216 prevent postoperative movement of the valve 222 following placement of the valve within the annulus 208. The collar portion is configured from a conductive material which is configured to provide thermal energy to the valve annulus 208, as shown in FIG. 20, during installation of the replacement valve 222. In this manner the heating ring 212 is integrated into the construction of the replacement valve 222 and eliminates the need for a separate structure for providing thermal energy to the valve annulus 208. Thermal treatment of the annulus causes the valve annulus to shrink about the spined collar portion 214, thus impaling itself upon the spines 216 and securely fixing the replacement valve 222 within the annulus 208.

FIG. 22(B–D) shows alternate configurations for spines 216 for placement on the collar portion 214 to improve placement of the valve 222 within the annulus 208. The different spine or hook configurations of FIG. 22(B–D) are designed to "seat" the spines 216 firmly within the tissue of the valve annulus once that the annulus is contracted about the collar portion 214. As shown, a clockwise partial rotation of the valve 222 caused the spines 216 to dig into the tissue of the annulus. The spines 216 may also includes a barb portion which prevents the valve 222 from rotating counterclockwise once the valve is seated.

Figure 23:
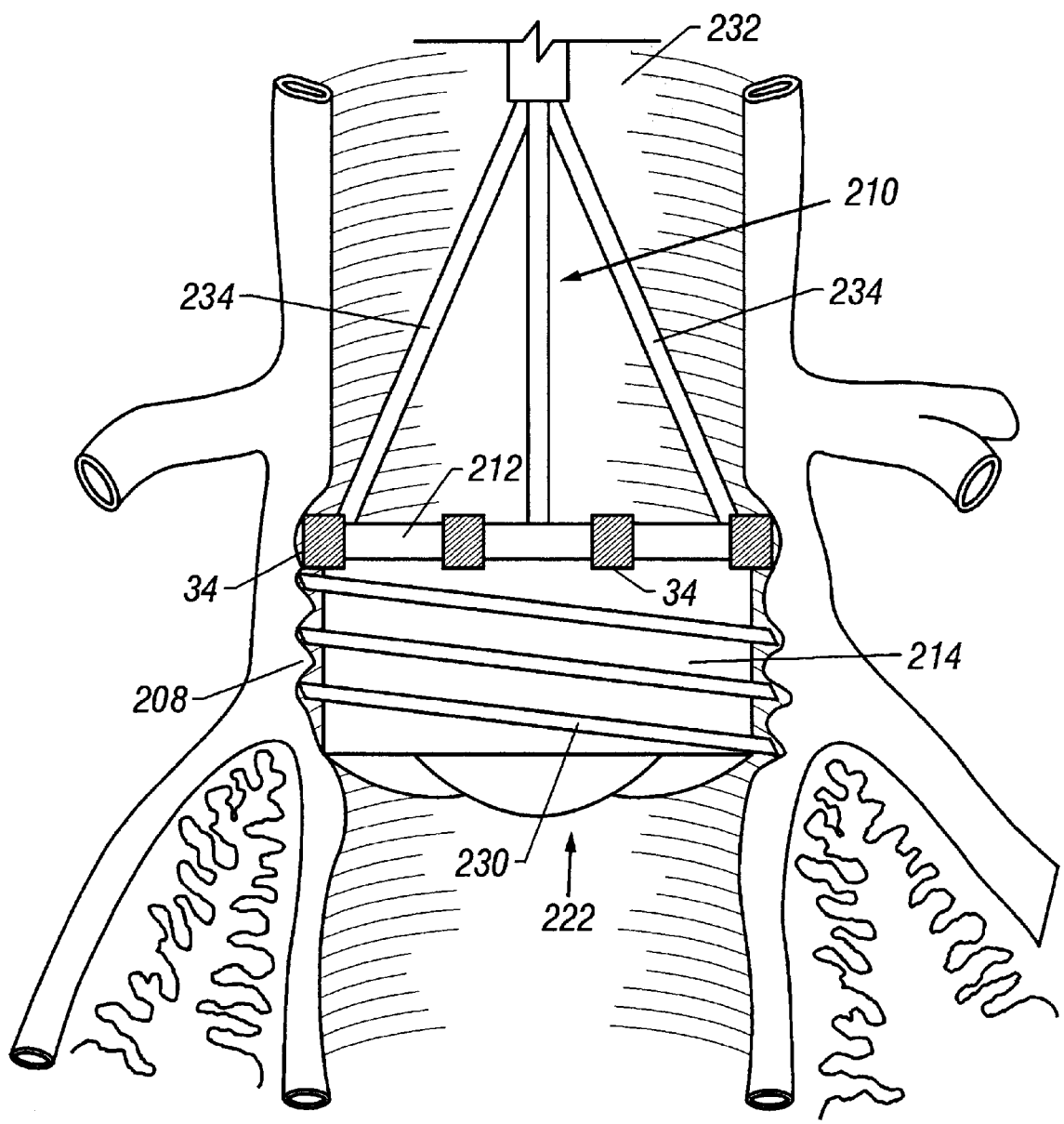
FIG. 23 shows an alternate configuration for a retaining means configured to prevent accidental dislodgement of the replacement valve from the annulus.

FIG. 23 shows an alternate configuration of the valve holder 210 for installing a replacement valve 222 within the valve annulus. The collar portion 214 includes a ridged thread 230 encircling the collar portion. The threaded portion function to prevent movement of the valve 222 within the annulus following installation of the valve 222. The threads also allow the valve 222 to be rotated in order to properly seat and orient the valve within the annulus. The threads may also allow the valve 222 to be removed and replaced without significant damage to the surrounding tissue should reoperation prove necessary.

In a preferred method of replacing the aortic valve, the aorta is dissected to provide access to the aortic valve at the upper portion of the left ventricle. Access to the aorta may be accomplished thorascopically, endovascularly, or using direct surgical techniques. The leaflets of the diseased valve are removed leaving the natural annulus of the valve in place. A thermal valve replacement device 200 is inserted into the aorta 232 so as to position a replacement valve 222 within the annulus 208 as shown in FIG. 19. In a preferred embodiment, the valve holder 210 comprises one or more arms 234 which fix the replacement valve 222 and heating ring 212 to the insertion member 206. The heating, ring 212 preferably includes a plurality of heating elements 34 which are in electrical communication with an external thermal energy source (not shown) via a wire element 238 running from the proximal end of the insertion member 206 and through the valve holder arm(s) 234.

Once the replacement valve 222 is properly placed relative to the valve annulus 208, thermal energy is supplied to the collagen tissue of the annulus 208 as shown in FIG. 20. The annulus 208 is caused to contract about the outer collar portion 214 of the replacement valve 222, fixing the valve 222 in place within the annulus 208. Spines 216 (as shown in FIGS. 22A–D), or threads (FIG. 23), or hooks may be used to further ensure that the replacement valve does not shift within the annulus 208.

Figure 21:
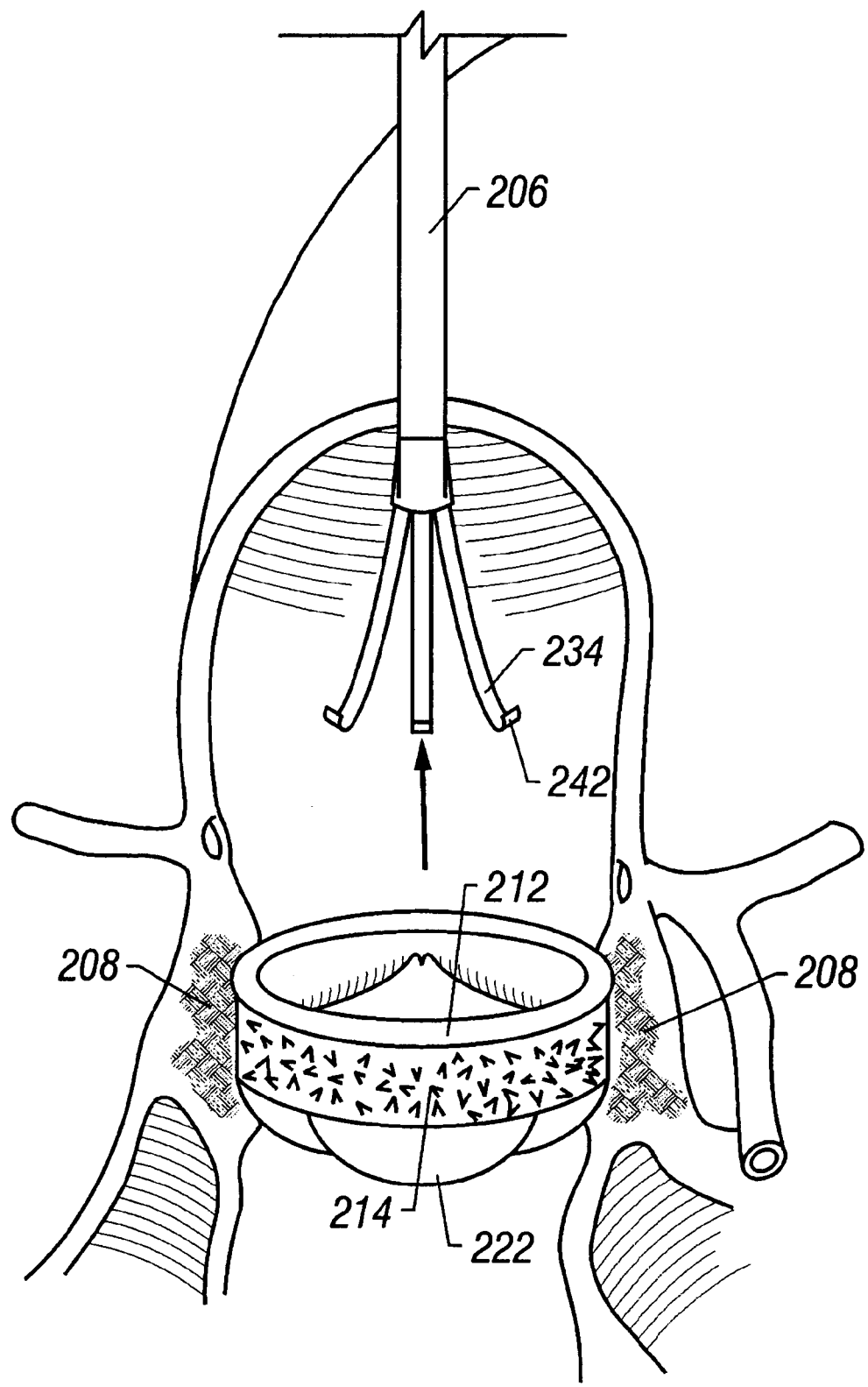
FIG. 21 shows the thermal valve replacement device of FIG. 20 being removed from the region of interest.

When the surgeon determines that the replacement valve 222 is properly placed within the annulus 208, the supply of thermal energy to the heating ring 212 is discontinued and the valve holder 210 is disconnected from the replacement valve as shown in FIG. 21. The arms 234 of the device 200 of FIG. 21 may be made rotatable relative to the axis of the insertion member 206 such that rotation of the arms 234 toward the axis of the insertion member 206 causes an engagement means 242 provided at the distal end of each arms 234 to disengage from the collar portion 214. The heating ring 212 may also be made removable from the collar portion 214 such that following placement of the device 200 within the annulus 208, the heating ring 212 may be disengaged and removed from the area of interest.

Figure 24:
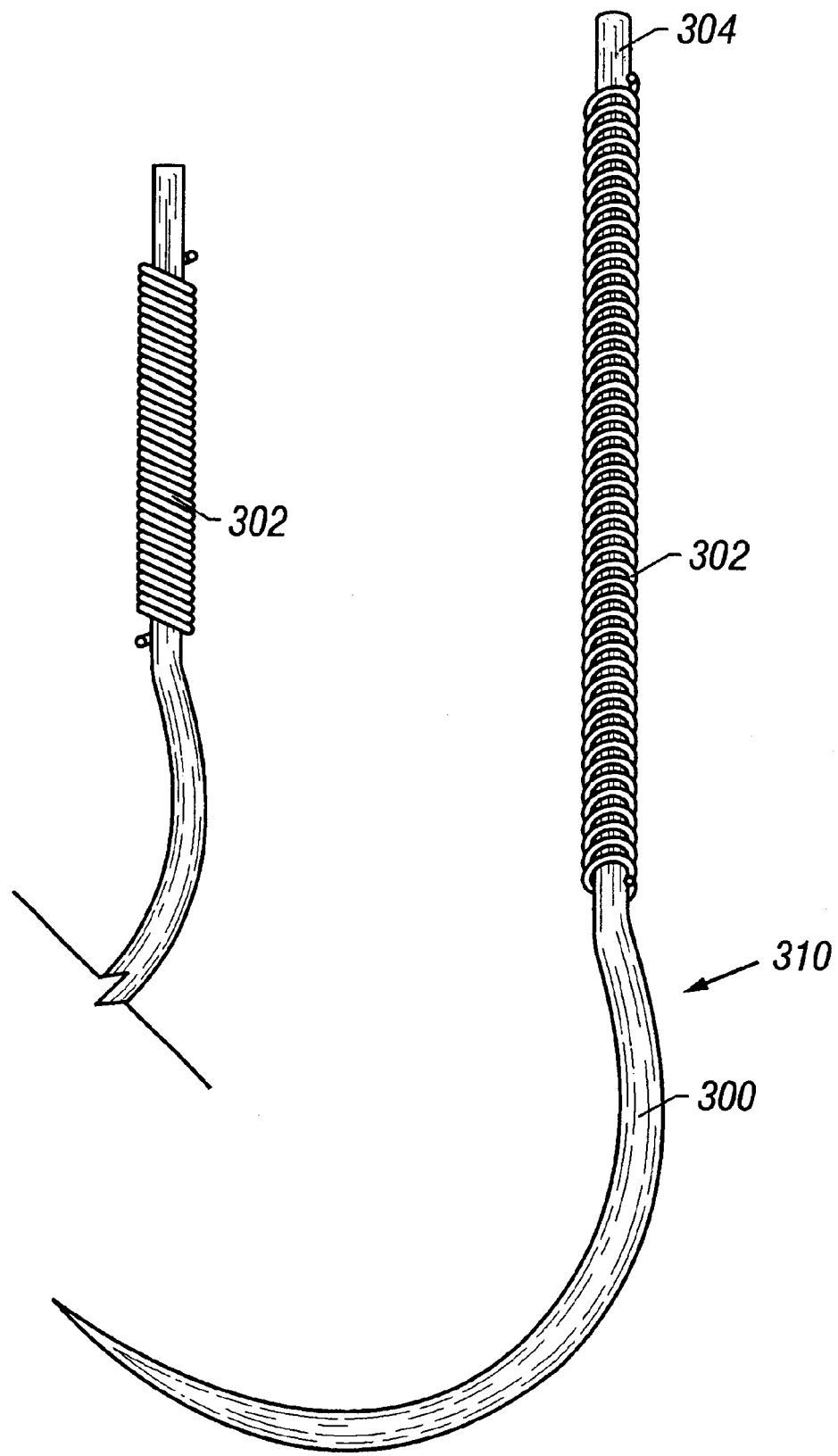
FIG. 24 is a thermal suture of the present invention configured to selectively apply thermal energy to a portion of a diseased heart valve.

A particular concern of valve repair and replacement surgery is ensuring precise, controlled shrinkage of the collagen tissue of the diseased valve. FIG. 24 shows a device of the present invention configured to precisely control the application of thermal energy to a collagen valve structure. The device of FIG. 24 comprises a thermal suture 310 having a sharpened needle member 300 configured for surgical applications. Attached to the proximal end of the needle member 300 is a thermally conductive thread member 404. A shank 302 is shown comprising a coiled thread of insulating material wherein the shank 302 is configured to prevent conductance from the thread member 310 to the needle member 300.

Figure 25:
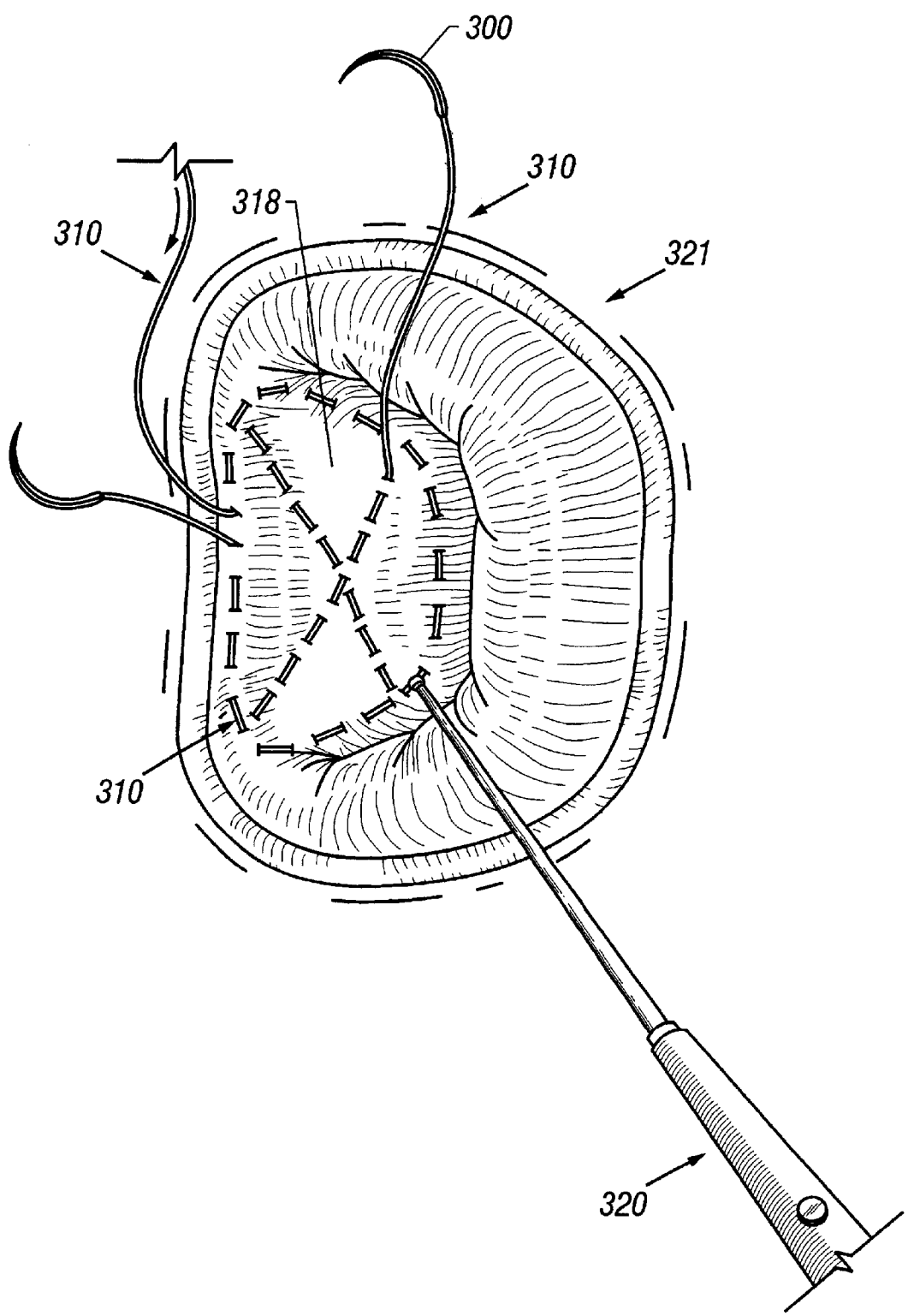
FIG. 25 shows a number of thermal sutures in place to selectively provide thermal energy to a diseased leaflet of a heart valve.

The thermal suture 310 is installed in the target tissue in similar fashion to a traditional suture, using any number of appropriate suturing techniques, including: simple interrupted, interrupted vertical mattress, interrupted horizontal mattress with or without pledgets, or continuous sutures. FIG. 25 shows a thermal suture 310 used to treat a leaflet 318 of a diseased mitral valve 321. The criss-cross pattern shown in FIG. 25 is intended to ensure equivalent shrinkage throughout the valve leaflet 318 so as to prevent inconsistent contraction of the leaflet 318 during treatment. A thermal wand 320 may be used to provide thermal energy to specific locations along the thermal suture 310. The surgeon can easily locate those locations wherein treatment would be most effective and provide thermal energy accordingly to the appropriate location along the thread member 304. It is also possible to provide thermal energy to one end of the thermal thread member 304 to accomplish treatment of the diseased valve. This may not be the most desirable means of controlling the supply of thermal energy to the collagen tissue as the amount of thermal energy supplied to the tissue declines along the length of the thread member 304 from the thermal energy source.

Figure 26:
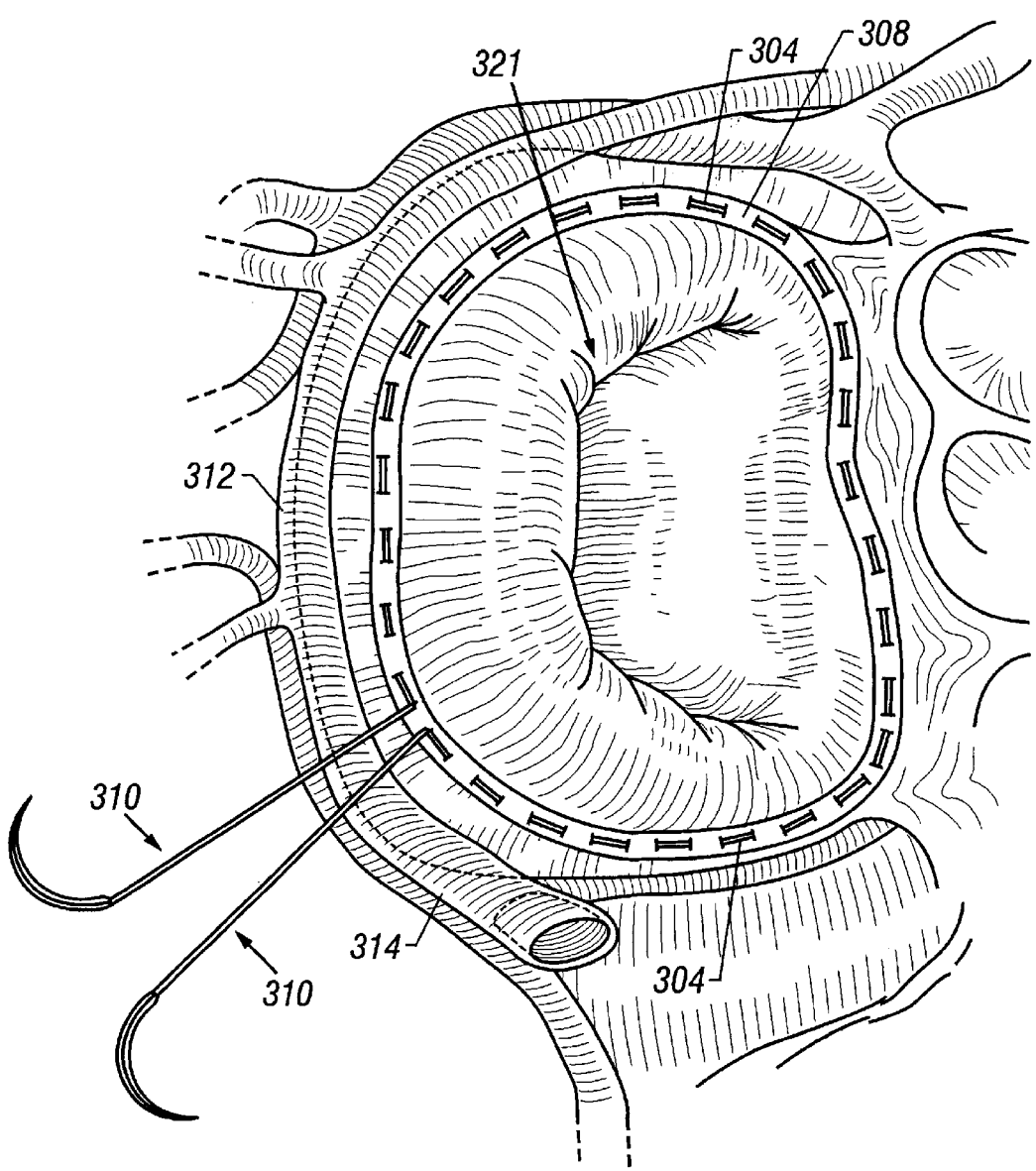
FIG. 26 shows a thermally conductive suture of the present invention in use to repair a diseased annulus of a heart valve.

Thermal repair of a diseased annulus is also possible with a thermal suture 310 of the present invention. As shown in FIG. 26, repair of a diseased annulus 308 of the mitral valve 321 may be accomplished by installing a thermal suture 310 along the periphery of the diseased annulus 308. A single suture 310 may be installed about the complete circumference of the annulus 308 or a number of sutures 310 may be installed at strategic locations about the circumference. The surgeon then selectively contracts the annulus 308 by providing thermal energy to specific locations on the thread member 304. Accordingly, the surgeon may restore the natural size and geometry of the annulus 308 so as to improve the fit of the valve leaflets and prevent regurgitation or prolapse of the valve. 321 Installation of the suture 10 in the annulus 308 of the valve 321 should be undertaken with considerable care to avoid penetrating the coronary sinus 312 or the coronary artery 314 during installation of the thermal suture 310.

In one method of the present invention, the sutures 310 may be installed on an initially cardioplegic heart. Following installation of the sutures 310 in the desired location and configuration, the heart is taken off cardioplegia and restarted. Once the heart is beating normally, a thermal wand 310 may be inserted endovascularly or percutaneously to a working space proximate the valve annulus 308. As described above, the valve performance may be monitored using TEE or other imaging techniques simultaneously with selectively providing thermal energy to the thread member 304. Thus, the surgeon is provided with real time feedback as to the effect of the thermal treatment so that he can precisely tailor the application of thermal energy to maximize the efficacy of the procedure.

Figure 27:
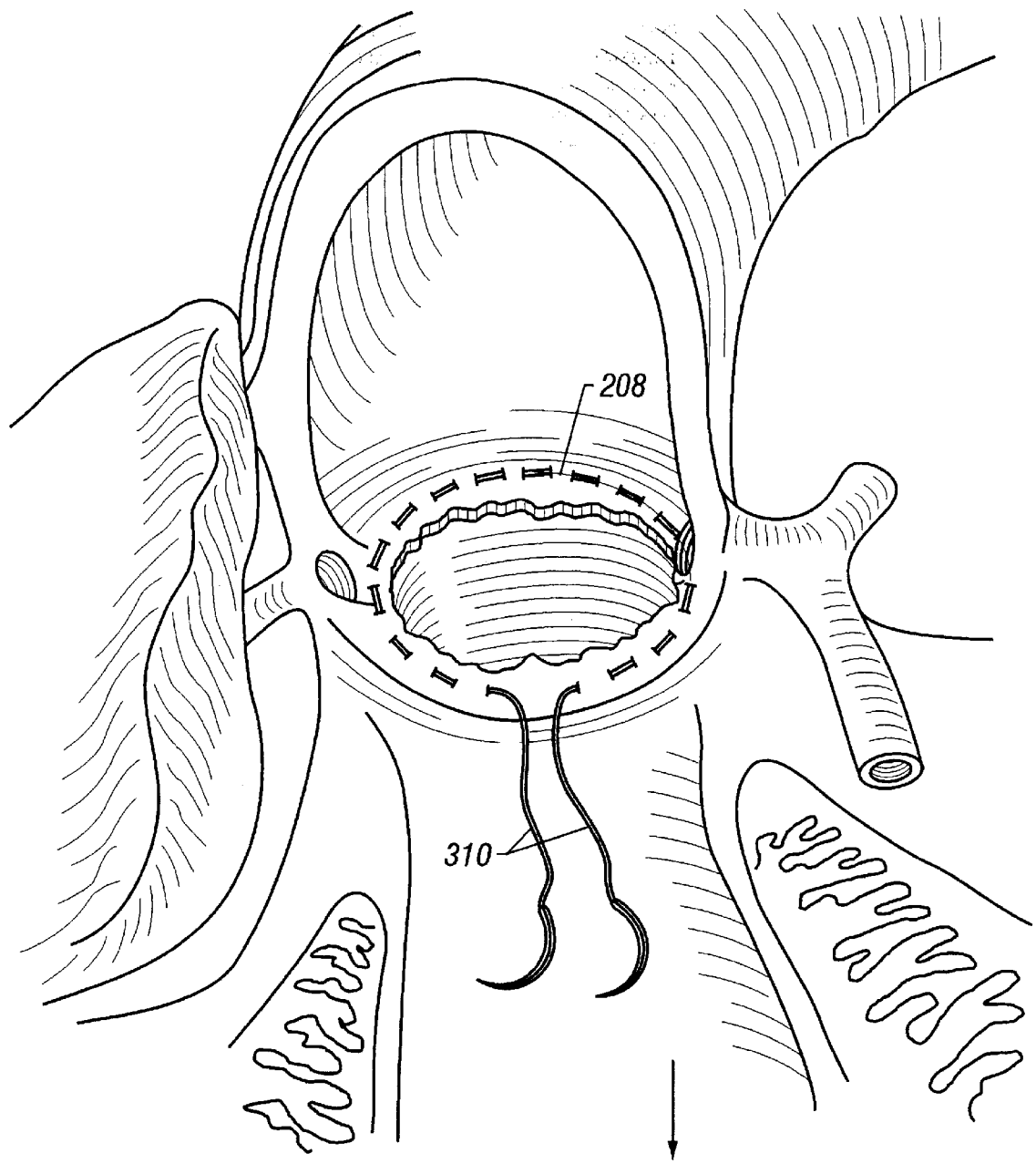
FIG. 27 shows a thermally conductive suture of the present invention in use to replace a diseased heart valve.

A thermal suture 310 of the present invention may also be used as an effective means of valve replacement. As shown in FIG. 27, one or more thermal sutures 310 are installed in a traditional fashion about the periphery of the valve annulus 208. A single suture 310 may be installed about the complete circumference of the annulus 208 or a number of sutures 310 may be installed at strategic locations about the circumference. The sutures may be installed in a continuous fashion or in a discrete number of loops about the annulus 208 depending on the clinical indications and the individual valve geometry.

Figure 28:
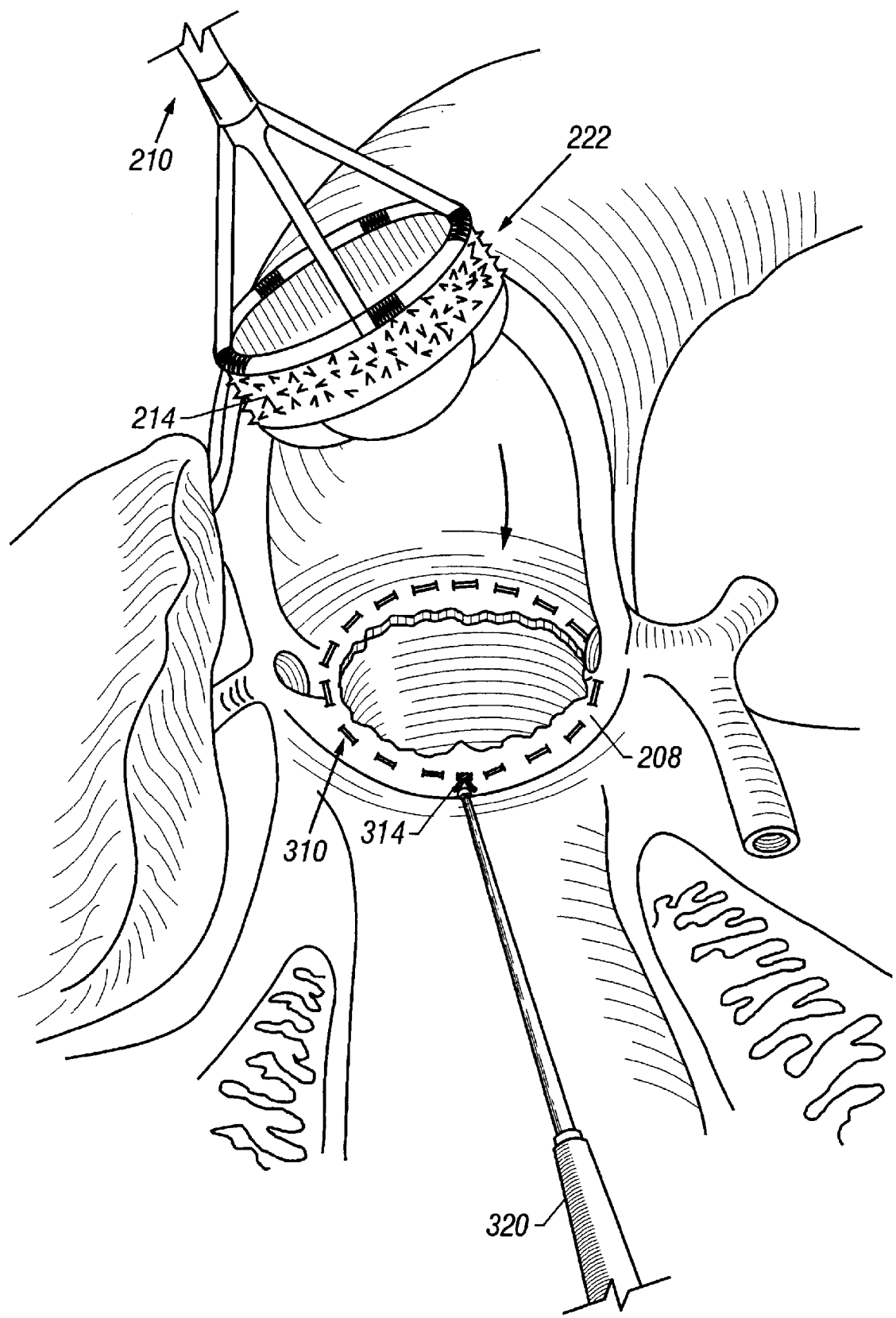
FIG. 28 illustrates the installation of a prosthetic heart valve using thermally conductive sutures of the present invention.
Figure 29:
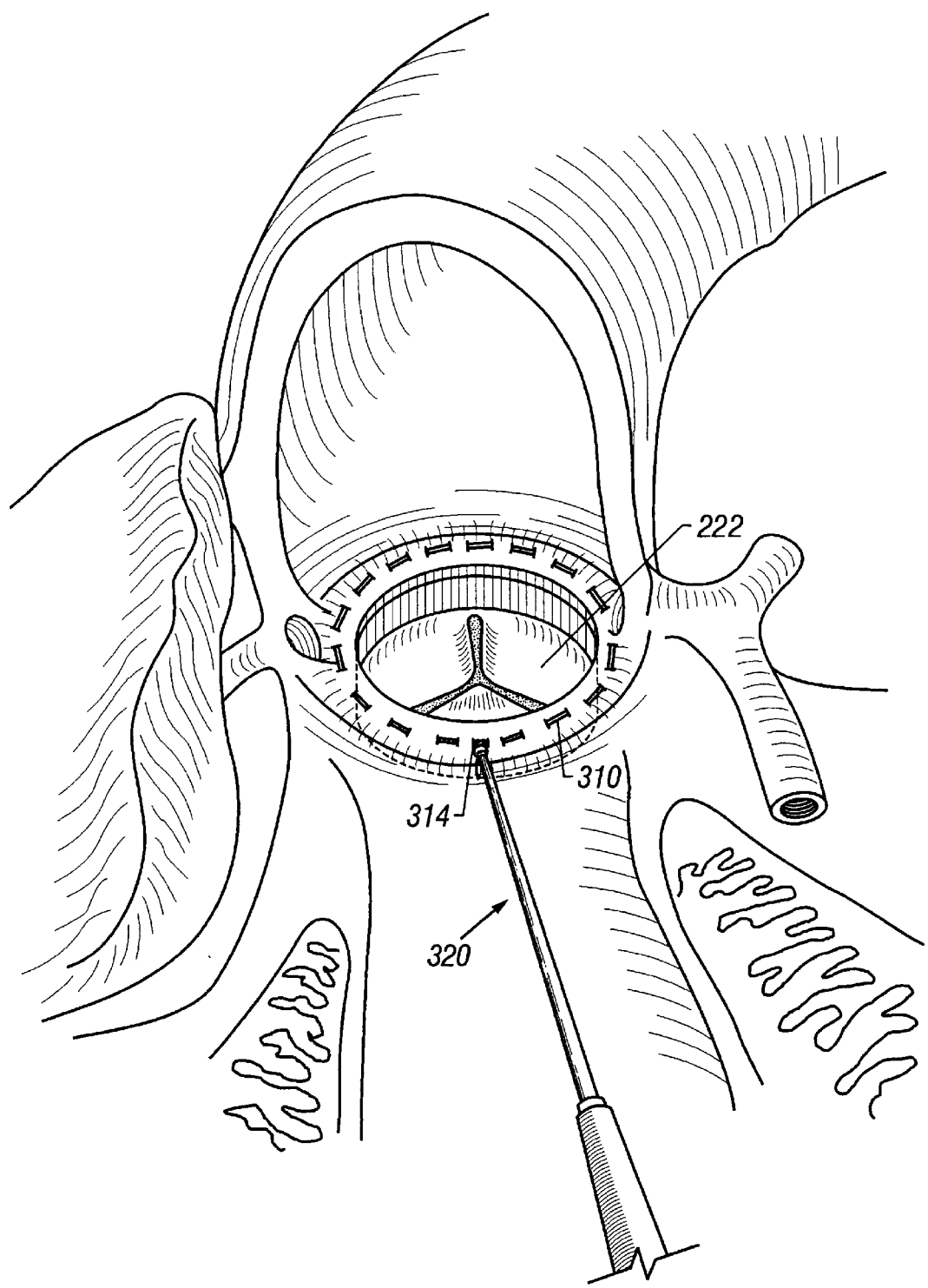
FIG. 29 illustrates the application of the thermal energy to the thermally conductive sutures in order to contract the valve annulus about a replacement prosthetic valve.

Either prior to or following the installation of the one or more thermal sutures 310 about the periphery of the valve annulus 208, the diseased leaflets are removed from the annulus 208 as described above, leaving the annulus intact. FIG. 27 shows the annulus 208 following installation of a single thermal suture 310 and removal of the leaflets of the valve. As shown in FIG. 28, a prosthetic valve 222, configured as described above, is inserted substantially even with and surrounded by the annulus 208. FIG. 28 shows a valve holder 210 of the present invention used to install a prosthetic valve 222 into the annulus 208 of the aortic valve.

Once the prosthetic valve 222 is properly positioned within the annulus 208 as shown in FIG. 28, thermal energy is selectively supplied to the thermal suture 310 from a thermal power source in thermal communication with the thermal suture 310. The thermal power source may be a thermal wand 320 used to contact the thermal thread member 304. The power source may also be directly attached to one or both ends of the thread member 304. The collagen tissue of the annulus 208 is thus contracted about the replacement valve 222, fixing the valve 222 firmly in place within the annulus 208. As described above, the prosthetic valve may include a collar 214 having an outer heart engaging surface comprising spines, ridges, hooks or other tissue engaging means configured to prevent accidental displacement of the valve 222 within the annulus 208. Following installation of the valve 222, the cardioplegic heart is restarted and access to he heart is closed.

Methods and devices for improving the performing of cardiac valves have been herein described. The particular examples set forth herein are instructional and should not be interpreted as limitations on the applications to which those of ordinary skill are able to apply this invention. Modifications and other uses are available to those skilled in the art, which are encompassed within the spirit and scope of the following claims.

What is claimed is:

1. An apparatus for supplying non-ablative thermal energy to a heart valve structure comprising:
   an elongate member having a distal end and a proximal end, the elongate member configured to allow insertion of the elongate member into a body vessel;
   a thermal heating member having a generally concave configuration shaped and proportioned to encompass generally oppositely disposed sides of the structure to be treated fixed to the distal end of the elongate member;
   at least one thermal heating element adapted to supply non-ablative thermal energy to a heart valve structure disposed on the thermal heating member; and
   a source of non-ablative energy in communication with the thermal heating element.

2. The apparatus of claim 1 wherein the at least one thermal heating element is an electrode in electrical communication with the energy source.

3. The apparatus of claim 1 wherein the thermal heating member includes a transverse groove sized to accommodate a valve chordae.

4. The apparatus of claim 1 including an integrally formed endoscope adapted to visualize an area of interest of the heart valve structure.

5. The apparatus of claim 1 wherein the elongate member includes a vacuum lumen in vacuum communication with a vacuum port disposed on the distal end of the elongate member.

6. The apparatus of claim 5 including a fiber-optic illuminator adapted to illuminate an area of interest on the heart valve structure.

7. The apparatus of claim 1 including a controller configured to selectively control the intensity and duration of thermal energy supplied to the thermal heating element.

8. The apparatus of claim 1 including a temperature sensor adapted to monitor the temperature of the thermal heating element.

9. The apparatus of claim 8 including a feedback control device configured to receive temperature data from the temperature sensor and adjust the supply of energy to the thermal heating element so as to maintain the temperature of the thermal heating element within a preselected temperature range.

10. The apparatus of claim 9 wherein the preselected temperature range is from 40° to 90° Celsius.

11. The apparatus of claim 1 including a lumen configured to supply conductive fluid to a heart valve structure to be treated.

12. The apparatus of claim 1 wherein the thermal heating member comprises a hook member sized to engage a valve chordae.

13. The apparatus of claim 12 wherein the hook member is conformable.

14. The apparatus of claim 1 wherein the elongate member and the thermal member are configured to be disposed within a trocar insertion sleeve.

15. The apparatus of claim 14 wherein the thermal heating member comprises a flexible panel member configured to be rolled lengthwise when disposed within the trocar insertion sleeve.

16. The apparatus of claim 14 wherein the elongate member includes a steering means located at the proximal end of the elongate member configured to manipulate at least the distal end of the elongate member.

17. The apparatus of claim 1 wherein the elongate member comprises a flexible cannula configured for endovascular insertion of the elongate member through a body vessel.

18. The apparatus of claim 1 wherein the elongate member comprises an elongate wand.

19. The apparatus of claim 1 wherein the at least one heating element is located on an inner surface of the thermal heating member.

20. An apparatus for supplying non-ablative thermal energy to a heart valve structure comprising:
    an elongate member having a distal end and a proximal end, the elongate member configured to allow insertion of the elongate member into a body vessel;
    a thermal heating member having a generally annular configuration fixed to the distal end of the elongate member;
    at least one thermal heating element adapted to supply non-ablative thermal energy to a heart valve structure disposed on the thermal heating member; and
    a source of non-ablative energy in communication with the thermal heating element.

21. The apparatus of claim 20 wherein the thermal heating member comprises an annular configuration sized to approximate the circumference of an annulus.

22. The apparatus of claim 21 wherein the annular configuration has a circumference of between 8.5 to 10 cm.

23. The apparatus of claim 21 wherein the thermal heating member is conformable.

24. The apparatus of claim 21 wherein the apparatus is adapted to be endovascularly delivered proximate the valve structure to be treated.

25. The apparatus of claim 21 wherein the at least one thermal heating element comprises a plurality of thermal heating elements disposed about a circumference of the thermal heating member.

26. The apparatus of claim 21 wherein the annular configuration is concentrically disposed about the elongate member.

27. The apparatus of claim 26 including a plurality of arms circumferentially fixed at a first end about the distal end of the elongate member and circumferentially fixed at a second end to the annular configuration.

28. The apparatus of claim 26 including a fluid impermeable membrane fluidly sealing a cross sectional area of the thermal heating member defined by an inner circumference of the annular configuration and an outer circumference of the elongate member.

29. The apparatus of claim 26 wherein the annular configuration is collapsible about the elongate member.

30. The apparatus of claim 26 including a trocar insertion sleeve adapted to be slidingly disposed about the annular configuration.

31. The apparatus of claim 20 wherein the heating member comprises:
    a centrally disposed perfusion tube having a perfusion lumen therethrough, the perfusion lumen fluidly connecting at least one perfusion port formed in a wall of the perfusion tube with a distal end of the perfusion lumen;

an annular configuration concentrically disposed about the perfusion tube and sized to approximate the circumference of an annulus, wherein the at least one thermal heating element comprises a plurality of thermal heating elements disposed about a circumference of the annular configuration; and a fluid impermeable membrane adapted to fluidly seal a cross sectional area defined by an inner circumference of the annular configuration and an outer circumference of the perfusion tube.

32. The apparatus of claim 31 wherein the perfusion lumen includes a one-way valve configured to prevent fluid flow from the distal end of the perfusion lumen to the at least one perfusion port.

33. The apparatus of claim 31 including an insertion catheter slidingly disposed about the perfusion tube.

34. The apparatus of claim 31 wherein the annular configuration is contractible about the perfusion tube.

35. The apparatus of claim 33 including a plurality of proximal arm members, each proximal arm member having a proximal end fixed to a distal end of the insertion catheter and a distal end fixed to the annular configuration, and a plurality of distal arm members, each distal arm member having a distal end fixed to the perfusion tube and a proximal end fixed to the annular configuration.

36. The apparatus of claim 20 wherein the at least one thermal heating element is an electrode in electrical communication with the energy source.

37. The apparatus of claim 20 including an integrally formed endoscope adapted to visualize an area of interest of the heart valve structure.

38. The apparatus of claim 20 wherein the elongate member includes a vacuum lumen in vacuum communication with a vacuum port disposed on the distal end of the elongate member.

39. The apparatus of claim 38 including a fiber-optic illuminator adapted to illuminate an area of interest on the heart valve structure.

40. The apparatus of claim 20 including a controller configured to selectively control the intensity and duration of thermal energy supplied to the thermal heating element.

41. The apparatus of claim 20 including a temperature sensor adapted to monitor the temperature of the thermal heating element.

42. The apparatus of claim 41 including a feedback control device configured to receive temperature data from the temperature sensor and adjust the supply of energy to the thermal heating element so as to maintain the temperature of the thermal heating element within a preselected temperature range.

43. The apparatus of claim 42 wherein the preselected temperature range is from 40° to 90° Celsius.

44. The apparatus of claim 20 including a lumen configured to supply conductive fluid to a heart valve structure to be treated.

45. The apparatus of claim 20 wherein the elongate member and the thermal member are configured to be disposed within a trocar insertion sleeve.

46. The apparatus of claim 45 wherein the elongate member includes a steering means located at the proximal end of the elongate member configured to manipulate at least the distal portion of the elongate member.

47. The apparatus of claim 20 wherein the elongate member comprises a flexible cannula configured for endovascular insertion of the elongate member through a body vessel.

48. The apparatus of claim 20 wherein the elongate member comprises an elongate wand.

49. The apparatus of claim 20 wherein the at least one heating element is located on an inner surface of the thermal heating member.

50. A method of treating a heart valve stricture comprising:

providing a working space proximate a heart valve structure; and providing non-ablative thermal energy to the heart valve structure so as to selectively contact at least a portion of the heart valve structure;

wherein said step of providing non-ablative thermal energy comprises inserting a thermal treatment apparatus into the working space proximate the structure, the thermal apparatus comprising an elongate member having a distal end and a proximal end, the elongate member configured to allow insertion of the elongate member into a body vessel; a thermal heating member having a generally concave configuration shaped and proportioned to encompass generally oppositely disposed sides of the structure to be treated fixed to the distal end of the elongate member; at least one thermal heating element adapted to supply non-ablative thermal energy to a heart valve structure disposed on the thermal heating member; and a source of non-ablative energy in communication with the thermal heating element.

51. The method of claim 50 wherein elongate member comprises a wand member configured to be percutaneously delivered to a region of interest proximate the heart valve structure, the step of providing a working space proximate the heart valve structure comprising performing a beating-heart endovascular access procedure.

52. The method of claim 50 wherein the step of contacting the valve structure with the thermal heating element of the thermal heating member comprises contacting an annulus of the heart valve.

53. The method of claim 52 wherein the step of selectively contracting the annulus causes a reduction in the circumference of the annulus.

54. The method of claim 50 including the additional step of monitoring the functioning of the heart valve with a monitoring device substantially simultaneously with providing thermal energy to the heart valve structure.

55. The method of claim 54 wherein the monitoring device comprises a transesophegial echocardiography device, the method including the additional step of installing the device so as to monitor the functioning of the heart valve.

56. The method of claim 50 wherein the step of providing a working space proximate the heart valve structure comprises performing an access procedure chosen from the group consisting of: a thoracotomy, a sternotomy, a mini-thoracotomy, a mini-sternotomy, a sub-xyphoid access procedure, a xyphoid access procedure, a thorascopic procedure, and an endovascular access procedure.

57. The method of claim 50 including the additional step of placing the heart on cardiopulmonary bypass prior to the step of providing a working space proximate the heart valve structure.

58. The method of claim 50 including the additional step of providing a thermally conductive fluid to at least a portion of the heart valve structure prior to the step of providing thermal energy from the thermal heating element.

59. A method of treating a heart valve structure comprising:

providing a working space proximate a heart valve structure; and providing non-ablative thermal energy to the heart valve structure so as to selectively contact at least a portion of the heart valve structure;

wherein said step of providing non-ablative thermal energy comprises inserting a thermal treatment apparatus into the working space proximate the structure, the thermal apparatus comprising an elongate member having a distal end and a proximal end, the elongate member configured to allow insertion of the elongate member into a body vessel; a thermal heating member having a generally annular configuration fixed to the distal end of the elongate member; at least one thermal heating element adapted to supply non-ablative thermal energy to a heart valve structure disposed on the thermal heating member; and a source of non-ablative energy in communication with the thermal heating element.

60. The method of claim 59 wherein elongate member comprises a wand member to be percutaneously delivered to a region of interest proximate the heart valve structure, the step of providing a working space proximate the heart valve structure comprising performing a beating-heart endovascular access procedure.

61. The method of claim 59 wherein the step of contacting the valve structure with the thermal heating element of the thermal member comprises contacting an annulus of the heart valve.

62. The method of claim 61 wherein the step of selectively contracting the annulus causes a reduction in the circumference of the annulus.

63. The method of claim 59 including the additional step of monitoring the functioning of the heart valve with a monitoring device substantially simultaneously with providing thermal energy to the heart valve structure.

64. The method of claim 63, wherein the monitoring device comprises a transesophegial echocardiography device, the method including the additional step of installing the device so as to monitor the functioning of the heart valve.

65. The method of claim 59 wherein the step of providing a working space proximate the heart valve structure comprises performing an access procedure chosen from the group consisting of: a thoracotomy, a sternotomy, a mini-thoracotomy, a mini-sternotomy, a sub-xyphoid access procedure, a xyphoid access procedure, a thoracoscopic procedure, and an endovascular access procedure.

66. The method of claim 59 including the additional step of placing the heart on cardiopulmonary bypass prior to the step of providing a working space proximate the heart valve structure.

67. The method of claim 59 including the additional step of providing a thermally conductive fluid to at least a portion of the heart valve structure prior to the step of providing thermal energy from the thermal heating element.

68. An apparatus for supplying non-ablative thermal energy to a heart valve structure comprising:

an elongate member having a distal end and a proximal end, the elongate member configured to allow insertion of the elongate member into a body vessel;

a thermal heating member having a generally concavedly curved or annular configuration fixed to the distal end of the elongate member;

at least one thermal heating element adapted to supply non-ablative thermal energy to a heart valve structure disposed on the thermal heating member; and a source of non-ablative energy in communication with the thermal heating element;

wherein the thermal heating member includes a transverse groove sized to accommodate a valve chordae.

69. An apparatus for supplying non-ablative thermal energy to a heart valve structure comprising:

an elongate member having a distal end and a proximal end, the elongate member configured to allow insertion of the elongate member into a body vessel;

a thermal heating member having a generally concavedly curved or annular configuration fixed to the distal end of the elongate member;

at least one thermal heating element adapted to supply non-ablative thermal energy to a heart valve structure disposed on the thermal heating member;

a source of non-ablative energy in communication with the thermal heating element; and an integrally formed endoscope adapted to visualize the area of interest of the heart valve structure.

70. An apparatus for supplying non-ablative thermal energy to a heart valve structure comprising:

an elongate member having a distal end and a proximal end, the elongate member configured to allow insertion of the elongate member into a body vessel, wherein the elongate member includes a vacuum lumen in vacuum communication with a vacuum port disposed on the distal end of the elongate member;

a thermal heating member having a generally concavedly curved or annular configuration fixed to the distal end of the elongate member;

at least one thermal heating element adapted to supply non-ablative thermal energy to a heart valve structure disposed on the thermal heating member; and a source of non-ablative energy in communication with the thermal heating element.

71. The apparatus of claim 70, including a fiber-optic illuminator adapted to illuminate an area of interest on the heart valve structure.

72. An apparatus for supplying non-ablative thermal energy to a heart valve structure comprising:

an elongate member having a distal end and a proximal end, the elongate member configured to allow insertion of the elongate member into a body vessel;

a thermal heating member having a generally concavedly curved or annular configuration fixed to the distal end of the elongate member;

at least one thermal heating element adapted to supply non-ablative thermal energy to a heart valve structure disposed on the thermal heating member;

a source of non-ablative energy in communication with the thermal heating element; and a lumen configured to supply conductive fluid to a heart valve structure to be treated.

73. An apparatus for supplying non-ablative thermal energy to a heart valve structure comprising:

an elongate member having a distal end and a proximal end, the elongate member configured to allow insertion of the elongate member into a body vessel;

a thermal heating member having a generally concavedly curved or annular configuration fixed to the distal end of the elongate member, wherein the thermal heating member comprises a hook member sized to engage a valve chordae;

at least one thermal heating element adapted to supply non-ablative thermal energy to a heart valve structure disposed on the thermal heating member; and a source of non-ablative energy in communication with the thermal heating element.

74. The apparatus of claim 73 wherein the hook member is conformable.

75. An apparatus for supplying non-ablative thermal energy to a heart valve structure comprising:
   an elongate member having a distal end and a proximal end, the elongate member configured to allow insertion of the elongate member into a body vessel;
   a thermal heating member having a generally concavedly curved or annular configuration fixed to the distal end of the elongate member;
   at least one thermal heating element adapted to supply non-ablative thermal energy to a heart valve structure disposed on the thermal heating member; and
   a source of non-ablative energy in communication with the thermal heating element;
   wherein the elongate member and the thermal heating member are configured to be disposed within a trocar insertion sleeve.

76. The apparatus of claim 75 wherein the thermal heating member comprises a flexible panel member configured to be rolled lengthwise when disposed within the trocar insertion sleeve.

77. The apparatus of claim 75 wherein the elongate member includes a steering means located at the proximal end of the elongate member configured to manipulate at least the distal portion of the elongate member.

78. An apparatus for supplying non-ablative thermal energy to a heart valve structure comprising:
   an elongate member having a distal end and a proximal end, the elongate member configured to allow insertion of the elongate member into a body vessel;
   a thermal heating member having a generally concavedly curved or annular configuration fixed to the distal end of the elongate member;
   at least one thermal heating element adapted to supply non-ablative thermal energy to a heart valve structure disposed on the thermal heating member; and
   a source of non-ablative energy in communication with the thermal heating element;
   wherein the thermal heating member comprises an annular configuration sized to approximate the circumference of an annulus.

79. The apparatus of claim 78 wherein the annular configuration has a circumference of between 8.5 to 10 cm.

80. The apparatus of claim 78 wherein the thermal heating member is conformable.

81. The apparatus of claim 78 wherein the apparatus is adapted to be endovascularly delivered proximate the valve structure to be treated.

82. The apparatus of claim 78 wherein the at least one thermal heating element comprises a plurality of thermal heating elements disposed about a circumference of the thermal heating member.

83. The apparatus of claim 78 wherein the annular configuration is concentrically disposed about the elongate member.

84. The apparatus of claim 83 including a plurality of arms circumferentially fixed at a first end about the distal end of the elongate member and circumferentially fixed at a second end to the annular configuration.

85. The apparatus of claim 83 including a fluid impermeable membrane fluidly sealing a cross sectional area of the thermal heating member defined by an inner circumference of the annular configuration and an outer circumference of the elongate member.

86. The apparatus of claim 83 wherein the annular configuration is collapsible about the elongate member.

87. The apparatus of claim 83 including a trocar insertion sleeve adapted to be slidingly disposed about the annular configuration.

88. An apparatus for supplying non-ablative thermal energy to a heart valve structure comprising:
   an elongate member having a distal end and a proximal end, the elongate member configured to allow insertion of the elongate member into a body vessel;
   a thermal heating member having a generally concavedly curved or annular configuration fixed to the distal end of the elongate member;
   at least one thermal heating element adapted to supply non-ablative thermal energy to a heart valve structure disposed on the thermal heating member; and
   a source of non-ablative energy in communication with the thermal heating element;
   wherein the heating member comprises a centrally disposed perfusion tube having a perfusion lumen therethrough, the perfusion lumen fluidly connecting at least one perfusion port formed in a wall of the perfusion tube with a distal end of the perfusion lumen, an annular configuration concentrically disposed about the perfusion tube and sized to approximate the circumference of an annulus, wherein the at least one thermal heating element comprises a plurality of thermal heating elements disposed about a circumference of the annular configuration, and a fluid impermeable membrane adapted to fluidly seal a cross sectional area defined by an inner circumference of the annular configuration and an outer circumference of the perfusion tube.

89. The apparatus of claim 88 wherein the perfusion lumen includes a one-way valve configured to prevent fluid flow from the distal end of the perfusion lumen to the at least one perfusion port.

90. The apparatus of claim 88 including an insertion catheter slidingly disposed about the perfusion tube.

91. The apparatus of claim 90 including a plurality of proximal arm members, each proximal arm member having a proximal end fixed to a distal end of the insertion catheter and a distal end fixed to the annular configuration, and a plurality of distal arm members, each distal arm member having a distal end fixed to the perfusion tube and a proximal end fixed to the annular configuration.

92. The apparatus of claim 88 wherein the annular configuration is contractible about the perfusion tube.

93. A method of treating a heart valve structure comprising:
   providing a working space proximate a heart valve structure; and
   providing non-ablative thermal energy to the heart valve structure so as to selectively contact at least a portion of the heart valve structure;
   wherein said step of providing non-ablative thermal energy comprises inserting a thermal treatment apparatus into the working space proximate the structure,
   the thermal apparatus comprising an elongate member having a distal end and a proximal end, the elongate member configured to allow insertion of the elongate member into a body vessel; a thermal heating member having a generally concavedly curved or annular configuration fixed to the distal end of the elongate member; at least one thermal heating element adapted to supply non-ablative thermal energy to a heart valve structure disposed on the thermal heating member; and a source of non-ablative energy in communication with the thermal heating element, and the elongate member comprises a wand member configured to be percutaneously delivered to a region of interest proximate the heart valve structure, the step of providing a working space proximate the heart valve structure comprising performing a beating-heart endovascular access procedure.

94. A method of treating a heart valve structure comprising:

providing a working space proximate a heart valve structure;

providing non-ablative thermal energy to the heart valve structure so as to selectively contact at least a portion of the heart valve structure; and monitoring the functioning of the heart valve with a monitoring device substantially simultaneously with providing thermal energy to the heart valve structure;

wherein said step of providing non-ablative thermal energy comprises inserting a thermal treatment apparatus into the working space proximate the structure, the thermal apparatus comprising an elongate member having a distal end and a proximal end, the elongate member configured to allow insertion of the elongate member into a body vessel; a thermal heating member having a generally concavedly curved or annular configuration fixed to the distal end of the elongate member; at least one thermal heating element adapted to supply non-ablative thermal energy to a heart valve structure disposed on the thermal heating member; and a source of non-ablative energy in communication with the thermal heating element.

95. The method of claim 94 wherein the monitoring device comprises a transesophegial echocardiography device, the method including the additional step of installing the device so as to monitor the functioning of the heart valve.

96. A method of treating a heart valve structure comprising:

providing a working space proximate a heart valve structure; and providing non-ablative thermal energy to the heart valve structure so as to selectively contact at least a portion of the heart valve structure;

wherein said step of providing non-ablative thermal energy comprises inserting a thermal treatment apparatus into the working space proximate the structure, the thermal apparatus comprising an elongate member having a distal end and a proximal end, the elongate member configured to allow insertion of the elongate member into a body vessel; a thermal heating member having a generally concavedly curved or annular configuration fixed to the distal end of the elongate member; at least one thermal heating element adapted to supply non-ablative thermal energy to a heart valve structure disposed on the thermal heating member; and a source of non-ablative energy in communication with the thermal heating element, and wherein the step of providing a working space proximate the heart valve structure comprises performing an access procedure chosen from the group consisting of: a thoracotomy, a sternotomy, a mini-thoracotomy, a mini-sternotomy, a sub-xyphoid access procedure, a xyphoid access procedure, a thorascopic procedure, and an endovascular access procedure.

97. An apparatus for supplying non-ablative thermal energy to a heart valve structure comprising:

an elongate member having a distal end and a proximal end, the elongate member configured to allow insertion of the elongate member into a body vessel;

a thermal heating member having a generally concavedly curved or annular configuration fixed to the distal end of the elongate member;

at least one thermal heating element adapted to supply non-ablative thermal energy to a heart valve structure disposed on the thermal heating member; and a source of non-ablative energy in communication with the thermal heating element;

wherein the elongate member comprises a flexible cannula configured for endovascular insertion of the elongate member through a body vessel.

98. An apparatus for supplying non-ablative thermal energy to a heart valve structure comprising:

an elongate member having a distal end and a proximal end, the elongate member configured to allow insertion of the elongate member into a body vessel;

a thermal heating member having a generally concavedly curved or annular configuration fixed to the distal end of the elongate member;

at least one thermal heating element adapted to supply non-ablative thermal energy to a heart valve structure disposed on the thermal heating member; and a source of non-ablative energy in communication with the thermal heating element;

wherein the elongate member comprises an elongate wand.

99. A method of treating a heart valve structure comprising:

providing a working space proximate a heart valve structure; and providing non-ablative thermal energy to the heart valve structure so as to selectively contact at least a portion of the heart valve structure;

wherein said step of providing non-ablative thermal energy comprises inserting a thermal treatment apparatus into the working space proximate the structure, the thermal apparatus comprising an elongate member having a distal end and a proximal end, the elongate member configured to allow insertion of the elongate member into a body vessel; a thermal heating member having a generally concavedly curved or annular configuration fixed to the distal end of the elongate member; at least one thermal heating element adapted to supply non-ablative thermal energy to a heart valve structure disposed on the thermal heating member; and a source of non-ablative energy in communication with the thermal heating element, and wherein the step of contacting the valve structure with the thermal heating element of the thermal heating member comprises contacting an annulus of the heart valve.

100. The method of claim 99, wherein the step of selectively contracting the annulus causes a reduction in the circumference of the annulus.

101. A method of treating a heart valve structure comprising:

providing a working space proximate a heart valve structure;

providing non-ablative thermal energy to the heart valve structure so as to selectively contact at least a portion of the heart valve structure; and placing the heart on cardiopulmonary bypass prior to the step of providing a working space proximate the heart valve structure;

wherein said step of providing non-ablative thermal energy comprises inserting a thermal treatment apparatus into the working space proximate the structure, the thermal apparatus comprising an elongate member having a distal end and a proximal end, the elongate member configured to allow insertion of the elongate member into a body vessel; a thermal heating member having a generally concavedly curved or annular configuration fixed to the distal end of the elongate member; at least one thermal heating element adapted to supply non-ablative thermal energy to a heart valve structure disposed on the thermal heating member; and a source of non-ablative energy in communication with the thermal heating element.

102. A method of treating a heart valve structure comprising:

providing a working space proximate a heart valve structure;

providing non-ablative thermal energy to the heart valve structure so as to selectively contact at least a portion of the heart valve structure; and providing a thermally conductive fluid to at least a portion of the heart valve structure prior to the step of providing thermal energy from the thermal heating element;

wherein said step of providing non-ablative thermal energy comprises inserting a thermal treatment apparatus into the working space proximate the structure, the thermal apparatus comprising an elongate member having a distal end and a proximal end, the elongate member configured to allow insertion of the elongate member into a body vessel; a thermal heating member having a generally concavedly curved or annular configuration fixed to the distal end of the elongate member; at least one thermal heating element adapted to supply non-ablative thermal energy to a heart valve structure disposed on the thermal heating member; and a source of non-ablative energy in communication with the thermal heating element.

* * * * *